(12) United States Patent
Claire-Zimmet et al.

(10) Patent No.: US 8,056,176 B2
(45) Date of Patent: Nov. 15, 2011

(54) TOOTHBRUSHES

(75) Inventors: Karen Lynn Claire-Zimmet, Waltham, MA (US); William Ralph Brown, Jr., Peabody, MA (US); Alexander Timothy Chenvainu, Sudbury, MA (US); Chris Blain, Petaluma, CA (US); Jens Uwe Stoerkel, Frankfurt (DE); Ulrich Pfeifer, Munzenberg (DE); Gerhard Schaefer, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 798 days.

(21) Appl. No.: 12/008,073

(22) Filed: Jan. 8, 2008

(65) Prior Publication Data

US 2008/0178401 A1     Jul. 31, 2008

Related U.S. Application Data

(60) Provisional application No. 60/897,376, filed on Jan. 25, 2007.

(51) Int. Cl.
*A61C 17/22* (2006.01)
*A46B 9/04* (2006.01)
*A46B 9/06* (2006.01)

(52) U.S. Cl. ............. 15/28; 15/22.1; 15/167.1; 15/188; 15/194; 15/110; 601/141; 601/142

(58) Field of Classification Search .................. 15/22.1, 15/28, 167.1, 186–188, 194, 207.2, 110, 15/117; 601/139, 141, 142; D4/101, 104, 108, 109, 111

See application file for complete search history.

(56) References Cited

U.S. PATENT DOCUMENTS

| | | | | |
|---|---|---|---|---|
| 2,088,839 | A | * | 8/1937 | Coney et al. ................. 15/167.1 |
| 3,103,027 | A | * | 9/1963 | Birch ............................... 15/110 |
| 3,230,562 | A | | 1/1966 | Birch |
| 4,288,883 | A | * | 9/1981 | Dolinsky ........................ 15/110 |
| 6,993,804 | B1 | | 2/2006 | Braun et al. |
| 7,137,163 | B2 | | 11/2006 | Gatzemeyer et al. |
| 7,174,596 | B2 | | 2/2007 | Fischer et al. |
| 7,354,112 | B2 | | 4/2008 | Fischer et al. |
| 7,445,295 | B2 | | 11/2008 | Fischer et al. |
| 7,458,647 | B2 | | 12/2008 | Fischer et al. |
| 7,520,571 | B2 | | 4/2009 | Fischer et al. |
| 2004/0154112 | A1 | | 8/2004 | Braun et al. |
| 2004/0177462 | A1 | | 9/2004 | Brown, Jr. et al. |
| 2009/0178220 | A1 | | 7/2009 | Fischer et al. |

FOREIGN PATENT DOCUMENTS

WO     03/055351     *     7/2003

OTHER PUBLICATIONS

PCT International Search Report dated Jun. 19, 2008.

* cited by examiner

*Primary Examiner* — Mark Spisich

(57) ABSTRACT

Toothbrushes are provided which have various features that may include one or more tooth cleaning elements having a variety of shapes and sizes, one or more gum treating elements having a variety of shapes and sizes, and/or one or more soft tissue/tongue treating elements having a variety of shapes and sizes.

21 Claims, 25 Drawing Sheets

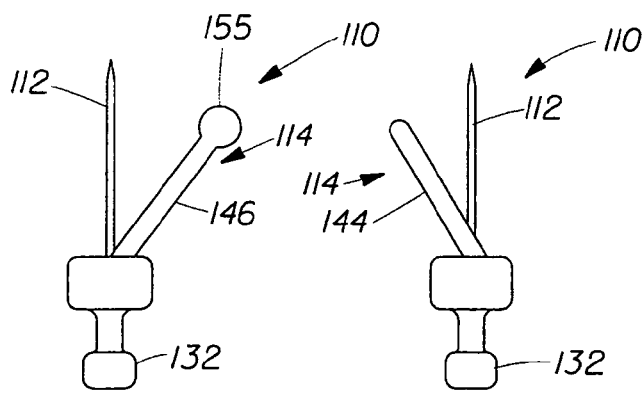
Fig. 27     Fig. 28     Fig. 29
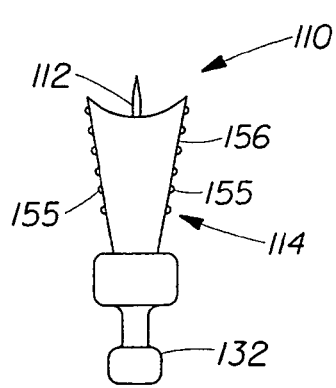     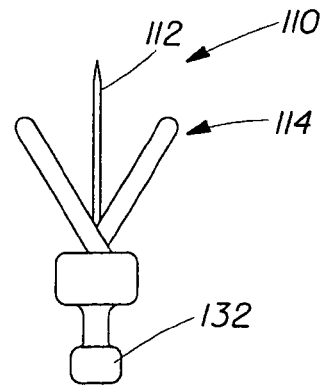     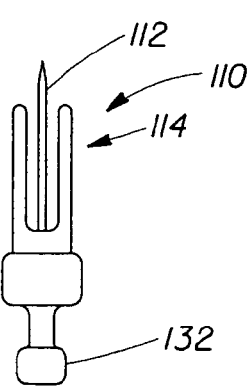
Fig. 30     Fig. 31     Fig. 32
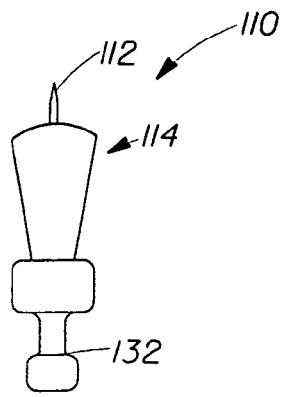
Fig. 33

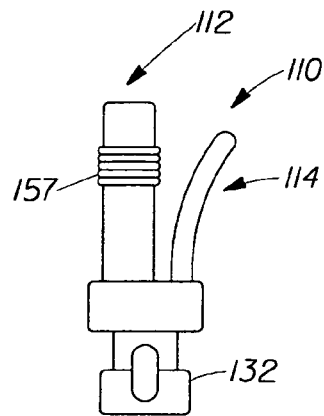
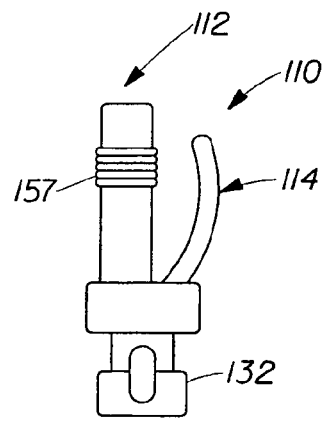
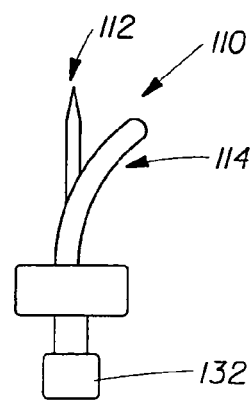
Fig. 35  Fig. 36  Fig. 37
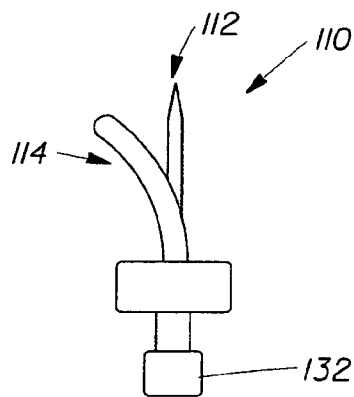
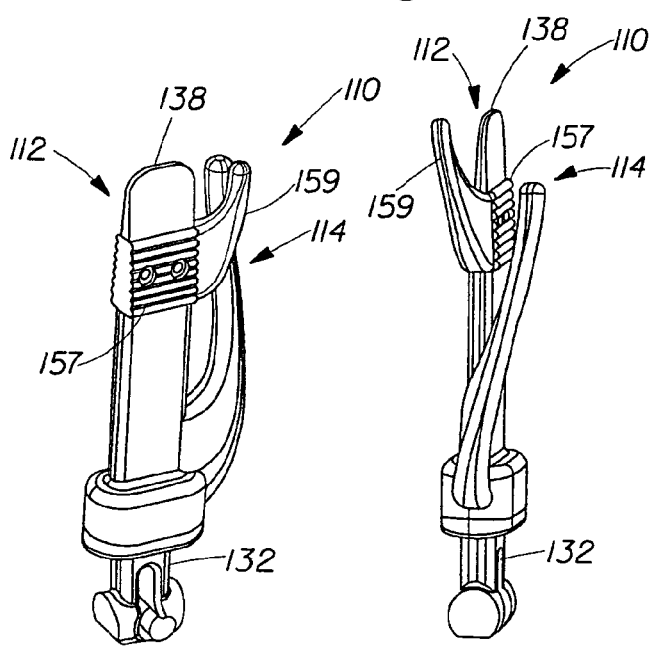
Fig. 38  Fig. 39  Fig. 40

TOOTHBRUSHES

CROSS REFERENCE TO RELATED APPLICATION

This application claims the benefit of U.S. Provisional Application No. 60/897376, filed Jan. 25, 2007, the substances of which are incorporated herein by reference.

FIELD OF THE INVENTION

This patent relates generally to the field of toothbrushes and to toothbrushes having various features that may include one or more tooth cleaning elements having a variety of shapes and sizes, one or more gum treating elements having a variety of shapes and sizes, and/or one or more soft tissue/tongue treating elements having a variety of shapes and sizes.

BACKGROUND OF THE INVENTION

While toothbrushes incorporating tooth cleaning elements having a variety of shapes are known, there is a continuing desire to provide toothbrushes, both manual and electric, having a variety of hard and soft tissue contacting elements that can provide one or more benefits.

BRIEF DESCRIPTION OF THE DRAWINGS

FIG. 27 is a side view of another composite structure of the present invention, wherein the side view of this composite element is shown as it would appear if disposed in the side view of the toothbrush head of FIG. 20;
FIG. 28 is a side view of another composite structure of the present invention, wherein the side view of this composite structure is shown as it would appear if disposed in the side view of the toothbrush head of FIG. 20;
FIG. 29 is a side view of another composite structure of the present invention, wherein the side view of this composite structure is shown as it would appear if disposed in the side view of the toothbrush head of FIG. 20;
FIG. 30 is a side view of another composite structure of the present invention, wherein the side view of this composite structure is shown as it would appear if disposed in the side view of the toothbrush head of FIG. 20;
FIG. 31 is a side view of another composite structure of the present invention, wherein the side view of this composite structure is shown as it would appear if disposed in the side view of the toothbrush head of FIG. 20;
FIG. 32 is a side view of another composite structure of the present invention, wherein the side view of this composite structure is shown as it would appear if disposed in the side view of the toothbrush head of FIG. 20;
FIG. 33 is a side view of another composite structure of the present invention, wherein the side view of this composite structure is shown as it would appear if disposed in the side view of the toothbrush head of FIG. 20;
FIG. 35 is a front view of another composite structure of the present invention;
FIG. 36 is a front view of another composite structure of the present invention;
FIG. 37 is a side view of another composite structure of the present invention;
FIG. 38 is a side view of another composite structure of the present invention;
FIGS. 39 and 40 are perspective views of another composite structure of the present invention.

DESCRIPTION

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 5:
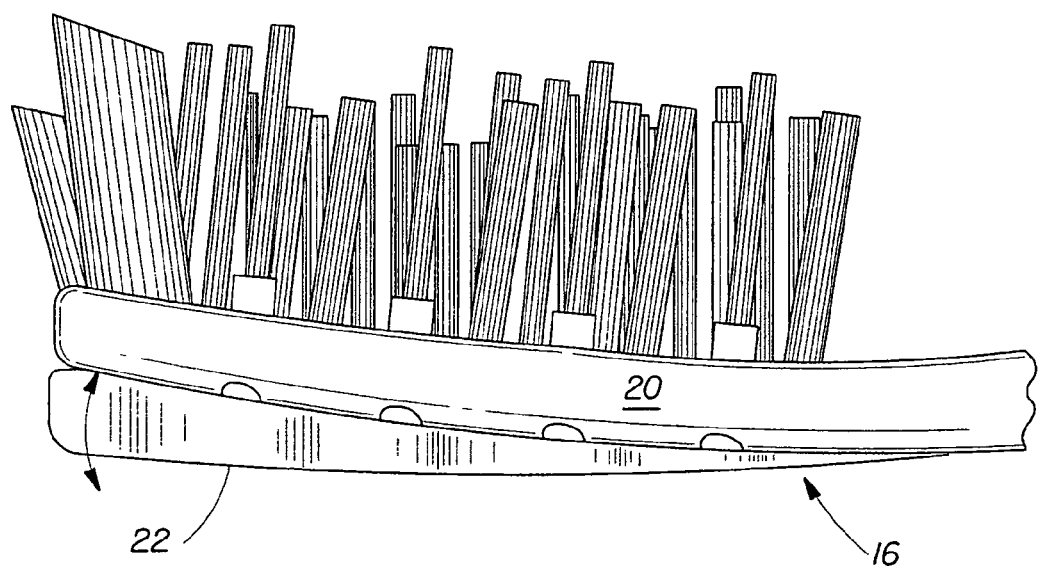
FIG. 5 is a side view of the head of FIG. 1 showing one of the head portions flexing.

Beginning with FIGS. 1-5, there is shown a toothbrush head 16 which extends from a neck 14 which extends from a handle (not shown) to form a toothbrush. The head and handle are preferably made of polypropylene. The head has a serpentine split 18 which divides the head into two portions 20 and 22. An end of the split 13 near neck 14 is preferably circular in shape (see FIG. 2). As shown in FIG. 5, the split in the head allows portions 20 and 22 to flex or move independent of each other during use of the toothbrush, thus facilitating cleaning of the teeth.

Split 18 can also be defined as an opening in the head between head portions 20 and 22. This opening allows water to flow through the head, thereby enhancing cleaning of the top head surface which typically gets caked with toothpaste in spite of efforts to rinse the head clean.

Head portion 20 includes a projecting part 24 which fits (at least partially) into a recess 26 (see FIG. 6) defined by portion 22. Projecting part 24 has several tufts of bristles extending from it (to be described in further detail below) and is surrounded on three sides by head portion 22.

Figure 2:
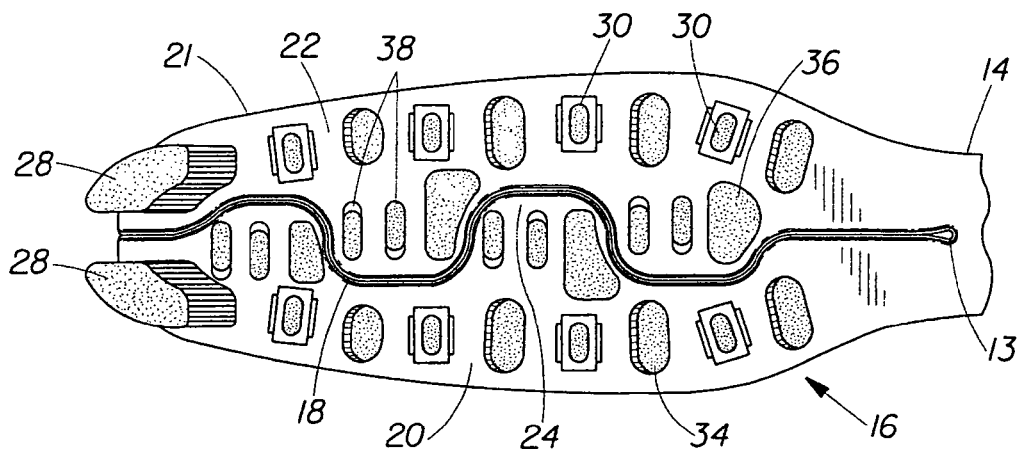
FIG. 2 is a top view of the head of FIG. 1.
Figure 3:
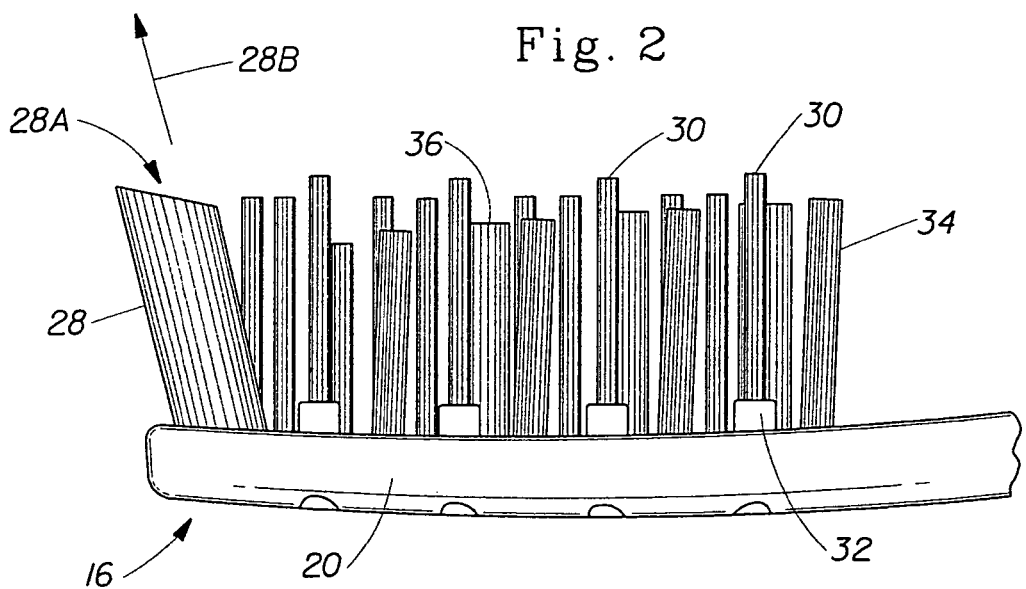
FIG. 3 is a side view of the head of FIG. 1.
Figure 4:
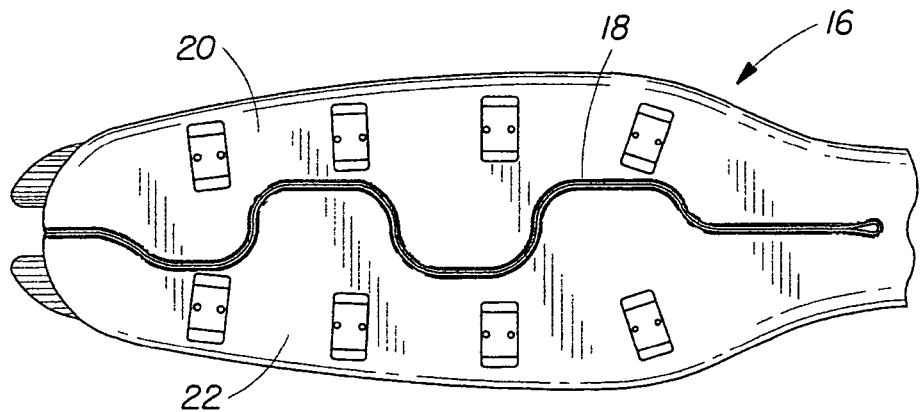
FIG. 4 is a bottom view of the head of FIG. 1.

Referring now to FIGS. 2 and 3, each of the tufts of bristles (tooth cleaning elements) on head 16 will be described. A first pair of tufts 28 are located towards the free end of the head, one on each head portion 20, 22. Each tuft has bristles (tooth cleaners) which preferably are each made of polybutyleneterephthalate (PBT) and have a diameter of 0.007 inches. The shortest bristles in tuft 28 have a length of 0.420 inches with the remaining bristles increasing in length steadily to a tip of the tuft. Each tuft tilts away from the handle by an angle of preferably about 12 degrees relative to that portion of the surface of the head from which it projects. As shown in FIG. 2, tufts 28 have a larger cross-section than any other tuft on the head.

A second group of tufts are pivoting tufts 30. There are four tufts 30 on each head portion 20, 22 which are located towards the outside of the head. Each tuft 30 can pivot up to about 15 degrees to either side of a vertical position on the head, more preferably being able to pivot up to about 8 degrees to either side of a vertical position on the head. The pivoting of tufts 30 is roughly towards or away from neck 14. Each tuft 30 includes a base support 32 made of polypropylene. The bristles are made of polyamide 6.12, have a diameter of 0.008 inches and extend 0.420 inches above the base support.

A third group of tufts 34 extend perpendicular to the head. There are four tufts 34 on each head portion 20, 22 which alternate with tufts 30. When viewed from the top (FIG. 2) the tufts are oval in shape (similar to tufts 30 but larger). In other words, the tufts 34 and 30 have oval shaped cross-sections. Each tuft 34 has bristles which are made of polyamide 6.12, have a diameter of 0.006 inches and extend above the head by about 0.385 inches.

A fourth group of tufts 36 are located towards the inside of the head. There are two such tufts on each head portion 20, 22. Each tuft 36 extends perpendicular to the head. The bristles of tuft 36 have a diameter of 0.006 inches, are made of polyamide 6.12 and rise about 0.360 inches above the head.

A fifth and final group of tufts 38 are also located towards the inside of the head (away from a perimeter 21 of the head). There are 4 pairs of tufts 38. In each pair one tuft is closer to neck 14 than the other tuft. In each pair of tufts 38, (a) a base of one tuft is closer to a first side of the head and this one tuft leans towards a second side of the head, and (b) a base of the other tuft is closer to the second side of the head and this other tuft leans towards the first side of the head. As such, the tufts in each pair lean across each other. The angle of tilt towards the side of the head is about five degrees. Each tuft 38 bristles which are made of PBT, have a bristle diameter of about 0.007 inches and extend about 0.460 inches above head 16. Each tuft 38 has an oval cross-section with a long dimension of the oval being oriented in the direction of tilt.

The bristles used on the head can be crimped (see U.S. Pat. No. 6,058,541) or notched (see U.S. Pat. No. 6,018,840). Other types of tooth cleaners besides bristles can be used. For example, a tuft of bristles could be replaced by an elastomeric fin. The US patents listed in this paragraph are incorporated herein by reference.

Figure 6:
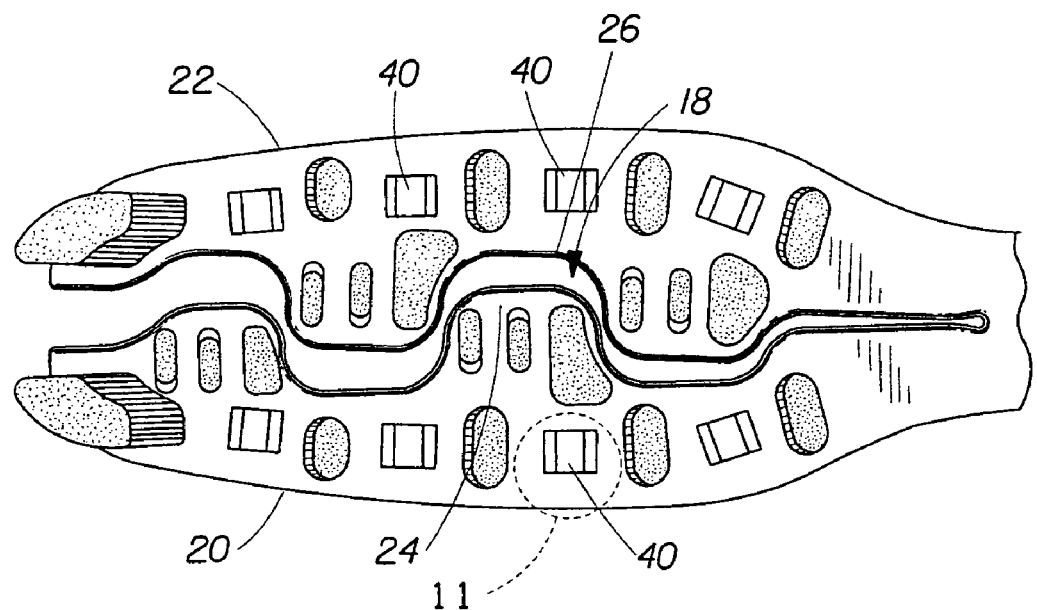
FIG. 6 is a top view of the head of FIG. 1 with the two head portions separated from each other.

Turning now to FIG. 6, a description will now be provided as to how the toothbrush (head) is made. In a first step, the head, neck and handle of the toothbrush are injection molded in a mold. During this injection molding step, tufts 28, 34, 36 and 38 are secured in the head by a hot-tufting process. Hot-tufting processes are well known by those skilled in the art (see, e.g., U.S. Pat. Nos. 4,635,313; and 6,361,120; British patent application 2,330,791; and European patent application 676,268 A1).

Briefly, hot-tufting involves presenting ends of a multiplicity of groups of plastic filaments into a mold. Each group of filament ends inside the mold is optionally melted into a blob. Each filament group is cut to a desired length (either before or after being introduced into the mold) to form a tuft of bristles. The mold is closed and molten plastic is injected into the mold. When the plastic solidifies, it locks one end of the tufts of bristles into the head of the toothbrush.

It can be seen in FIG. 6 that the opening 18 between head portions 20 and 22 is much wider at this point than in the heads final form (see FIG. 2). In other words, head portions 20 and 22 are spaced a predetermined distance (preferably at least about 1 mm) from each other. Further, through holes 40 are created during the molding step for receiving pivoting tufts 30 at a later point in the manufacturing process. Holes 40 will be described in greater detail below.

Figure 7:
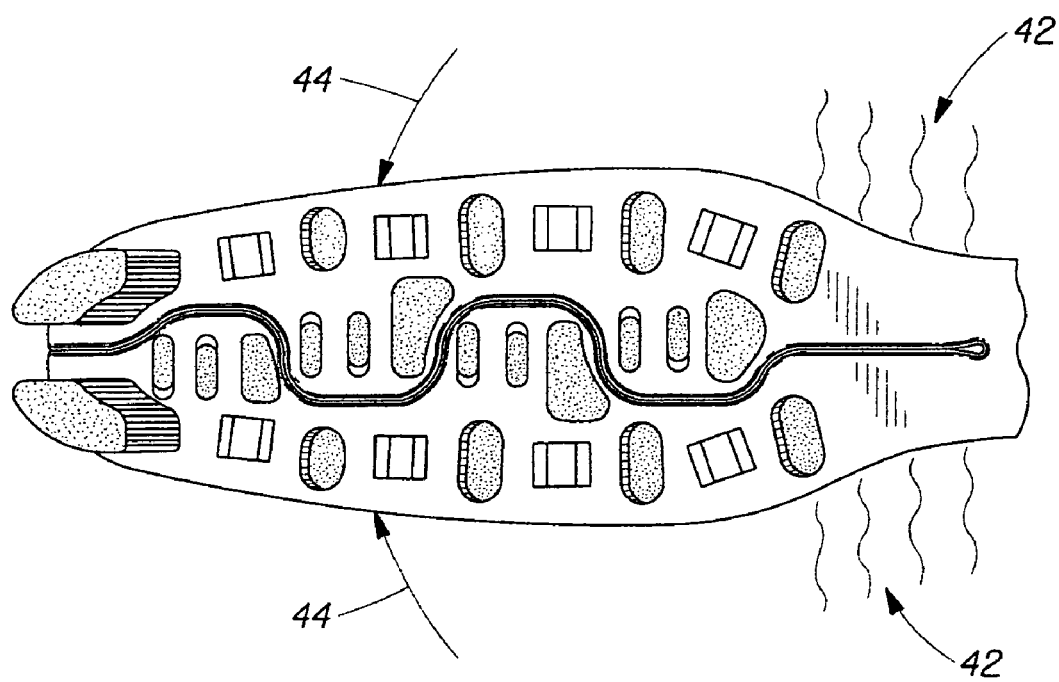
FIG. 7 is a top view of the head of FIG. 1 after the head portions have been positioned closer to each other.

With reference to FIG. 7, after the toothbrush is removed from the mold, heat 42 is applied to the head near the neck and to part of the neck (hereinafter the neck). The heat can be applied in a number of ways including hot air, radiant heating, ultrasonic or convection (e.g. hot oil) heating. Here the heat is shown being applied to the sides of the neck. It is preferable to apply the heat to the top and bottom surface of the neck. The heat brings the plastic up to 1.0-1.12 times its glass transition temperature (when temperatures are measured in the Kelvin scale). The plastic should not be heated above 1.12 times its glass transition temperature in order to avoid damaging the plastic. More preferably, the plastic is heated to about 1.03-1.06 times its glass transition temperature (measured in degrees Kelvin). The glass transition temperature for polypropylene is about 100 degrees centigrade whereas the glass transition temperature for copolyester and polyurethane is about 65 degrees centigrade.

Pressure 44 is then applied to head portions 20, 22 to move the portions towards each other. Once head portions 20, 22 are in the position shown in FIG. 2, the heated portion of the head/neck is cooled by, for example, exposing the heated portion to a cold gas or liquid. If room temperature air is used to cool the neck, such air should be applied for about 20-25 seconds. This has the effect of forming the two head portions into their final positions.

In order to achieve short process times, the highest temperature heat source which will not damage the plastic should be used. If too hot a heat source is used and/or if the heat is applied for too long, the plastic can be damaged. If the heat source is not hot enough, the process will take too long and/or head portions 20, 22 will not remain in their final desired positions. If the head/neck are made of polypropylene and hot air is used to heat the neck, (a) the heated air should be at a temperature of about 170 degrees centigrade and should be applied to the neck for about 70 seconds, (b) the polypropylene should be raised to a temperature of about 140 degrees centigrade, and (c) a nozzle which applies the hot air to the neck should be about 10 mm from the neck.

If copolyester or polyurethane is used as the material for the head neck, (a) the heated air should be at a temperature of 250 degrees centigrade and should be applied to the neck for about 10 seconds, (b) the material should be raised to a temperature of preferably 95-100 degrees centigrade, and (c) a nozzle which applies the hot air to the neck should be about 15-20 mm from the neck.

Heating the respective materials above for the time indicated allows the material to be softened and mechanically bent into its final form. Exceeding the heating times above could cause the material to overheat and become damaged.

Figure 8:
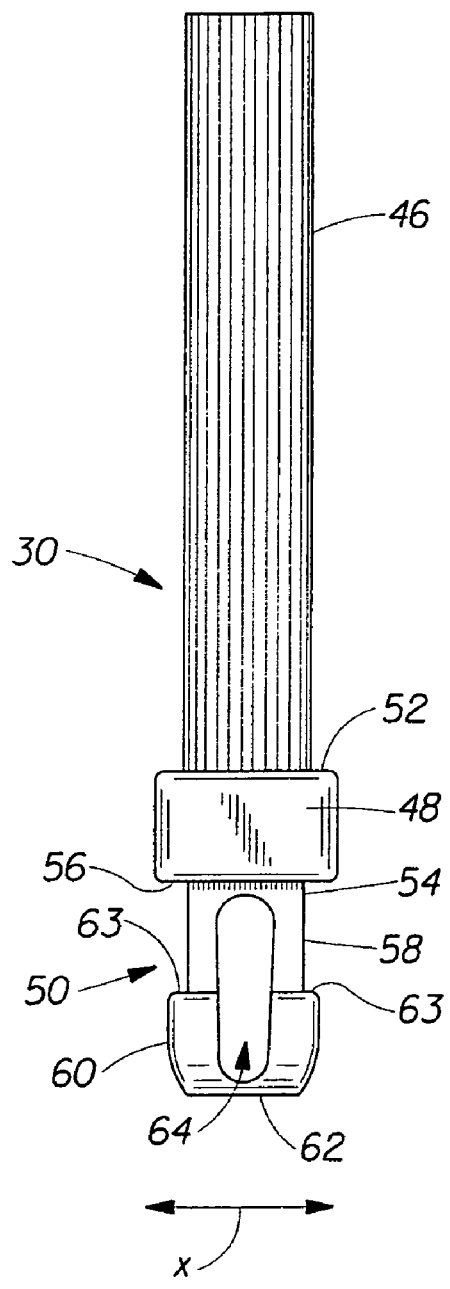
FIG. 8 is a front view of a pivoting tuft.
Figure 9:
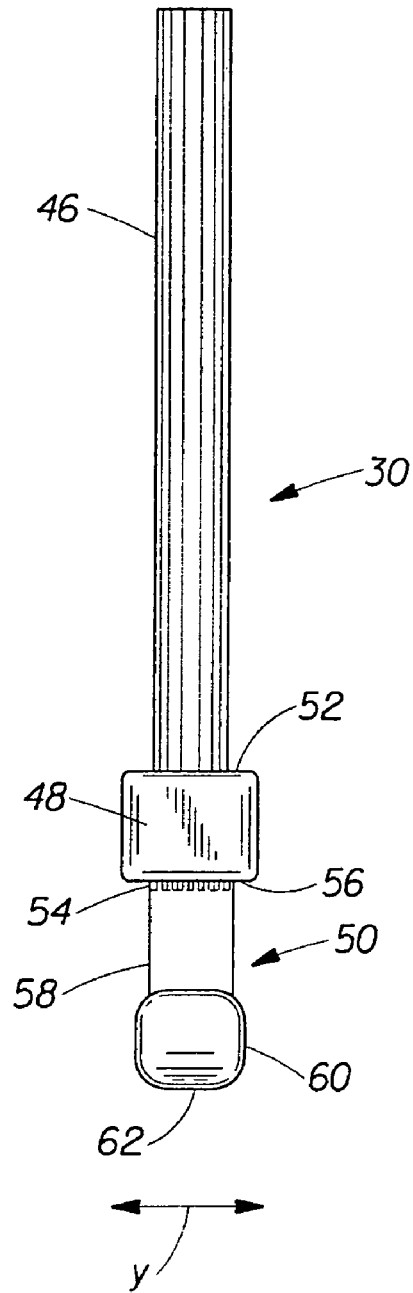
FIG. 9 is a side view of the pivoting tuft of FIG. 8.

Turning to FIGS. 8 and 9, each pivoting tuft 30 has a multiplicity of bristles 46, a base support 48 and an anchor pivot 50. The bristles are secured to and extend from a first end 52 of the base support while a first end 54 of the anchor pivot extends from a second end 56 of the base support. The base support and anchor pivot are preferably a unitary structure made of the same material. Anchor pivot 50 includes a first portion 58 near the first end 54 and a second portion 60 near a second end 62 of the anchor pivot. First portion 58 is smaller in an X an Y dimension than second portion 60. Base support 48 is larger in an X and Y dimension than second portion 60 of the anchor support. Second portion 60 includes a pair of lips 63. The anchor pivot defines an opening 64 therethrough.

Tuft 30 can also be made by a hot-tufting type process as described above. Instead of injecting plastic into the mold to form a toothbrush handle, neck and head, the plastic is injected into a mold to form base support 48 and anchor pivot 50, capturing bristles 46 when the injected plastic cools.

Figure 10:
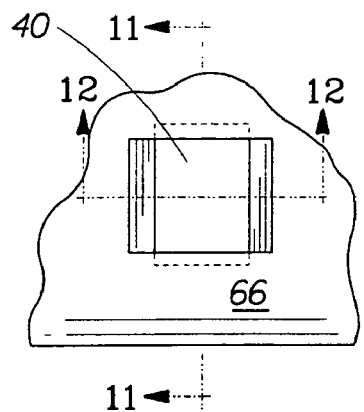
FIG. 10 is a top view of one of the holes in the head for receiving the pivoting tuft (see FIG. 6)
Figure 11:
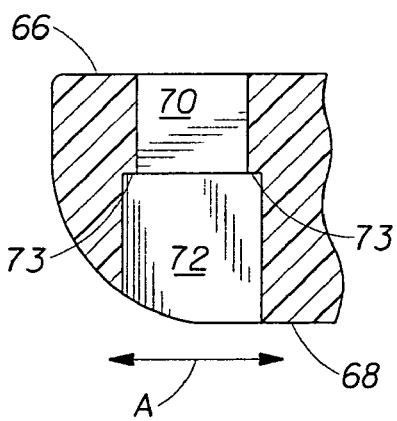
FIG. 11 is a sectional view of FIG. 10 taken along lines 11-11.
Figure 12:
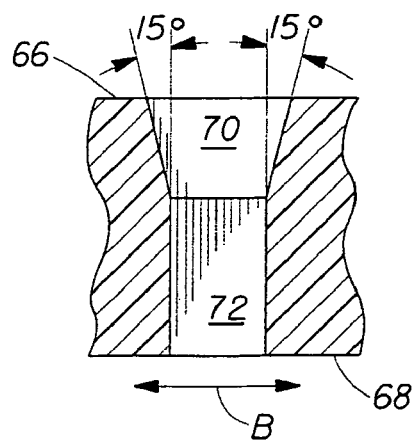
FIG. 12 is a sectional view of FIG. 10 taken along lines 12-12.

With reference to FIGS. 10-12, through holes 40 (FIG. 6) will now be described. Each hole 40 extends from a top surface 66 of the brush head through a bottom surface 68. Hole 40 includes first and second portions 70 and 72. Portion 72 is substantially a parallelepiped except that some of its lower section is rounded off (see FIG. 11). Portion 70 is also substantially a parallelepiped except that two of its sides are flared to the sides by about 15 degrees (see FIG. 12). Hole portion 72 is longer in a dimension A than hole portion 70 (FIG. 11). Hole portion 70 has about the same width in a dimension B as hole portion 72 where hole portions 70 and 72 meet (FIG. 12). Dimensions A and B are substantially perpendicular to each other in this embodiment. A pair of lips 73 are defined by this arrangement.

Figure 13:
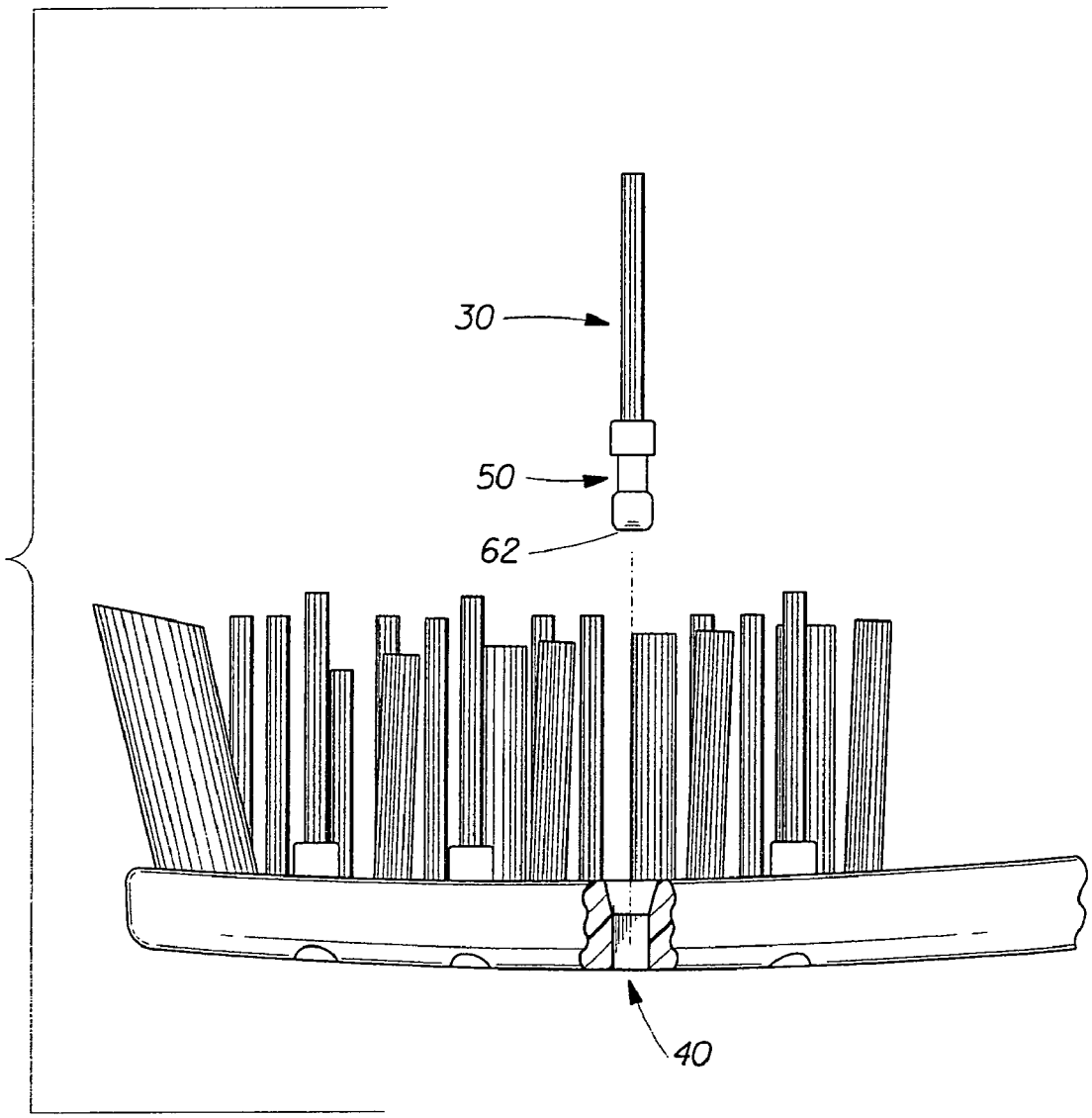
FIG. 13 is a side view of the head of FIG. 1 (a portion is removed to facilitate viewing) and a pivoting tuft prior to insertion into the head.
Figure 14:
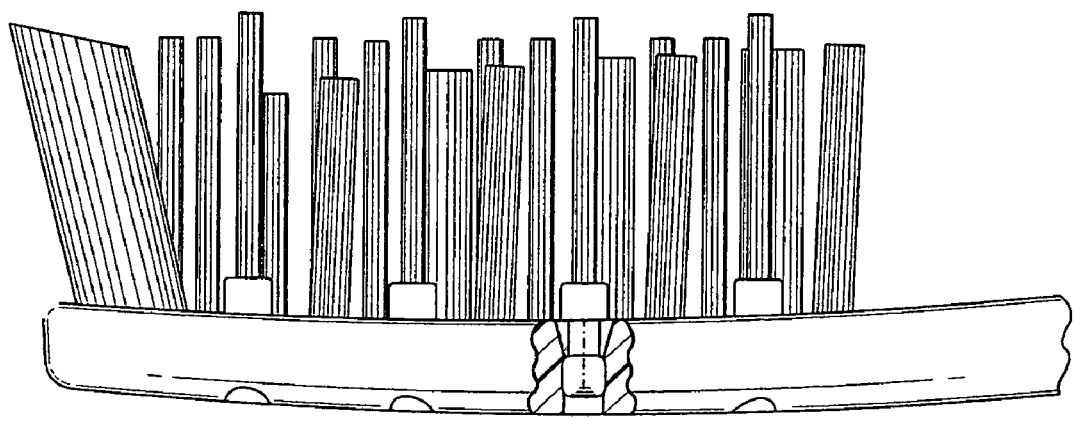
FIG. 14 is a side view of the head of FIG. 1 (a portion is removed to facilitate viewing) and a pivoting tuft after insertion into the head.

Turning now to FIGS. 13-16, the insertion of pivoting tufts 30 into holes 40 will be described. A tuft 30 is positioned over a hole 40 with end 62 of anchor pivot 50 facing the hole (FIG. 13). As shown in FIGS. 16A-C, tuft 30 is moved towards hole 40 until end 62 starts to enter the hole (FIG. 16A). Tuft 30 is then pressed into the hole causing sides of hole portion 70 to squeeze second portion 60 of the anchor pivot. Accordingly, anchor pivot 50 collapses causing opening 64 to become temporarily smaller. Tuft 30 is then pushed all the way into hole 40 (FIG. 16C) at which point the resilient plastic anchor pivot springs back to its form shown in FIG. 16A. This paragraph describes a snap-fit retention of tuft 30 to the head.

Figure 16A:
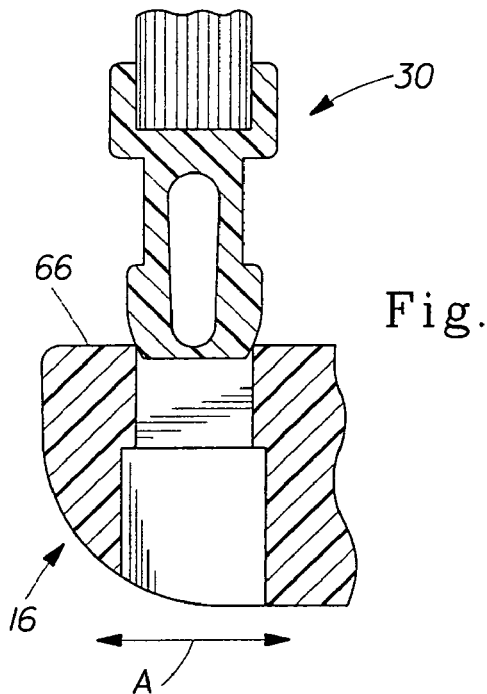
FIGS. 16A-C are sectional views of FIG. 15 taken along the lines 16A-C-16A-C.
Figure 16B:
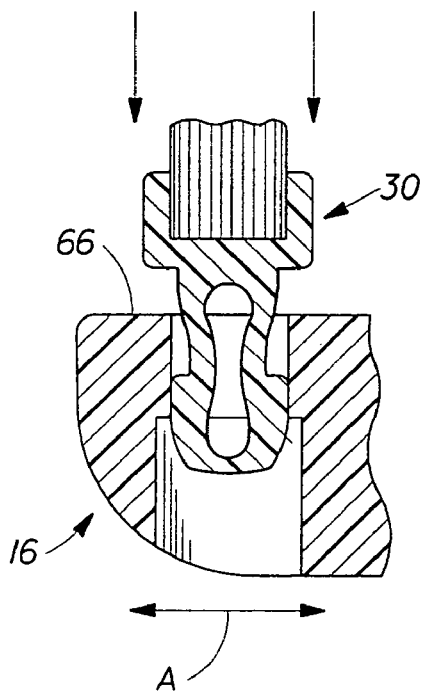
Figure 16C:
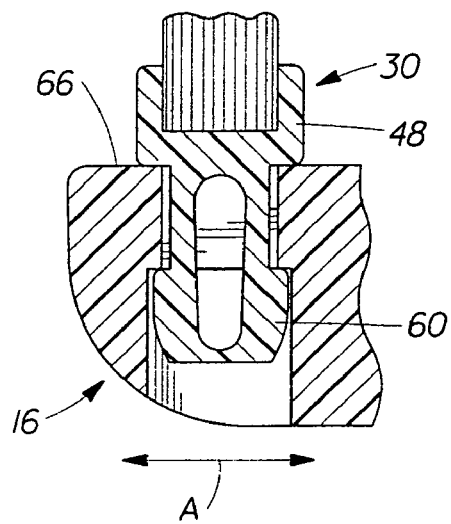

Referring to FIG. 16C, base support 48 is longer in the A dimension than hole portion 70 and thus prevents tuft 30 from being pressed further into hole 40. Second portion 60 is also longer in the A dimension than hole portion 70 and so prevents tuft 30 from moving back out of hole 40. This is due to the fact that lips 63 (FIG. 8) engage lips 73 (FIG. 11). This arrangement also prevents tuft 30 from rotating about the long axis of the bristles.

Figure 15:
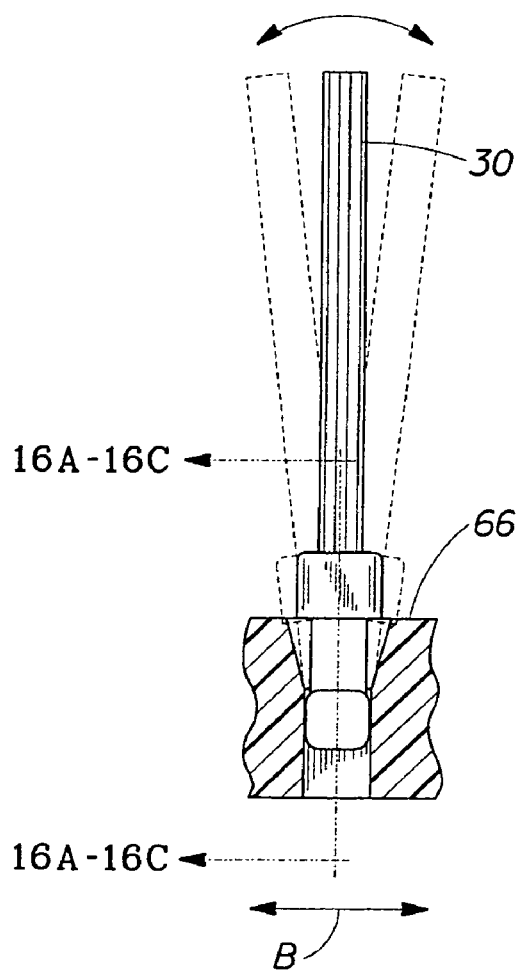
FIG. 15 is a side view of the pivoting tuft showing its motion.

As shown in FIG. 15, tuft 30 pivots when it is engaged by, for example, portions of the oral cavity during brushing. Preferably each tuft 30 can pivot up to about 15 degrees to either side of a position perpendicular to surface 66.

Figure 17:
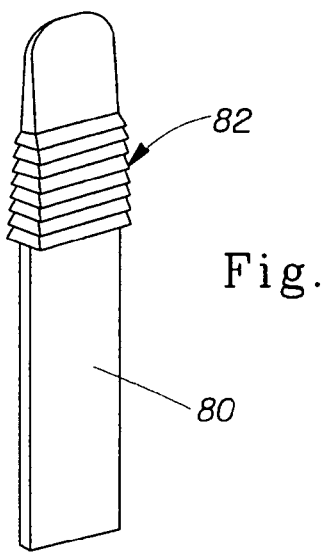
FIG. 17 is a perspective view of a tooth cleaner in the form of a ribbed fin.
Figure 18:
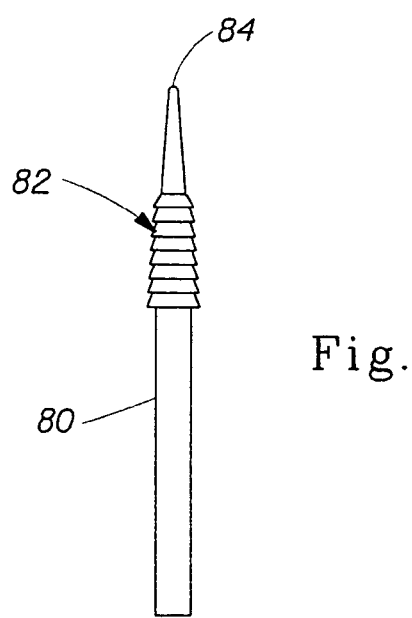
FIG. 18 is a side view of the ribbed fin of FIG. 17.

Turning to FIGS. 17 and 18, another type of tooth cleaning element in the form of a fin 80 is disclosed. Each fin is supported by a base support 48 and an anchor pivot 50 (both not shown) as described above, allowing the fin to pivot on the brush head. Alternatively, a fin can be securely affixed to the head so that it does not pivot. The fin is created of a thermoplastic elastomer (TPE) by an injection molding process. In this embodiment, a textured surface is provided by a series of ribs 82. These ribs enhance cleaning of the oral cavity. The ribs may be formed by injection molding a TPE over the fin. The ribs are preferably softer than the fin, but may be molded from the same material. Alternative textured surfaces (e.g. dimples) can be used in place of the ribs. As shown in FIG. 18, the fin has a width between about 1 mm and about 3 mm.

Figure 1:
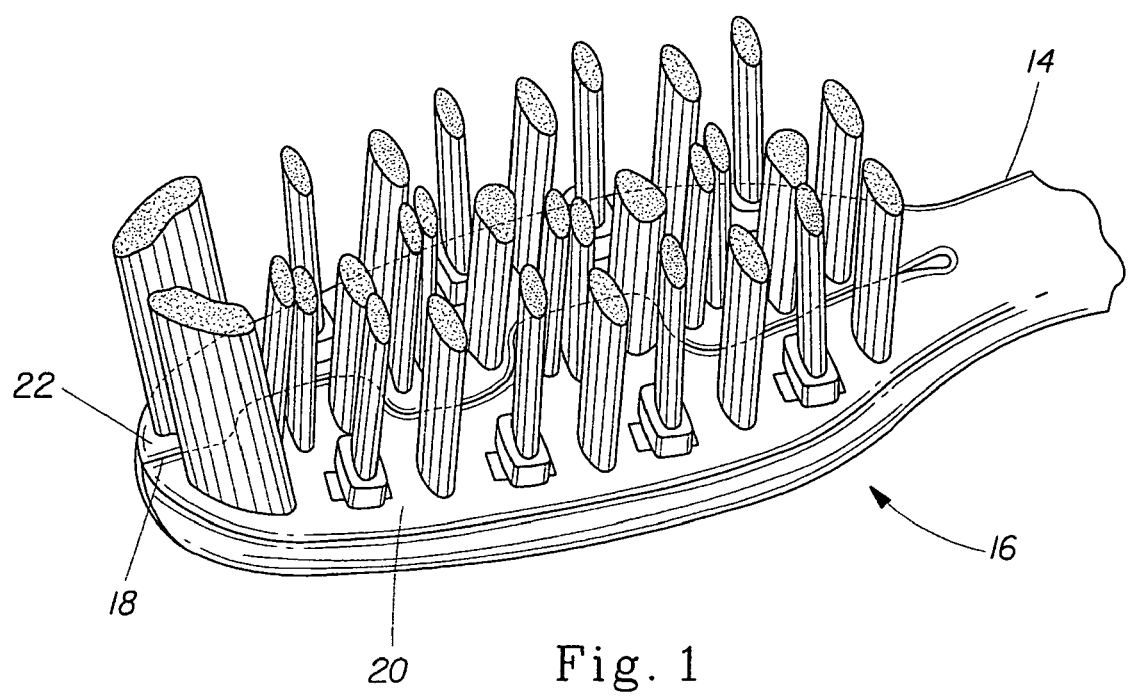
FIG. 1 is a perspective view of a toothbrush head.
Figure 19:
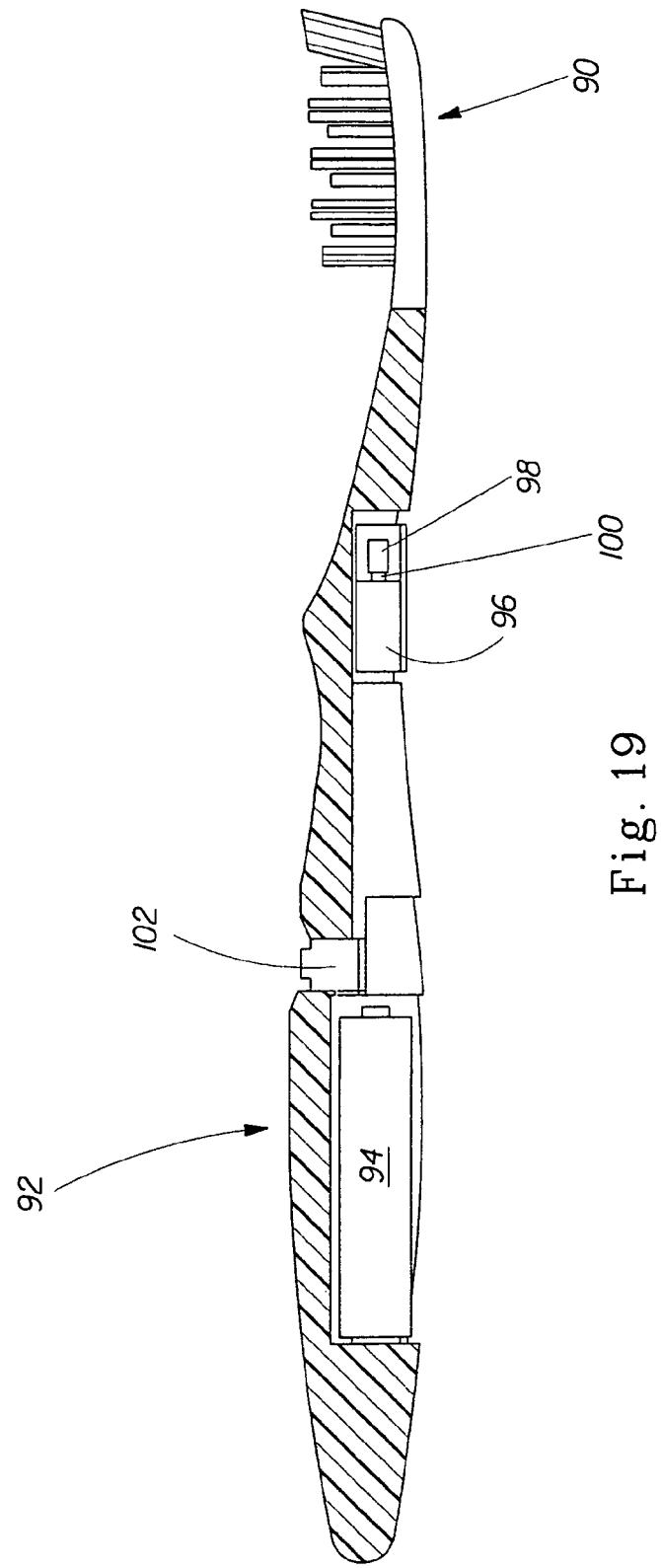
FIG. 19 is a side view in partial section of a toothbrush disclosing another embodiment of the invention.

FIG. 19 is a partial sectional view of a toothbrush showing another embodiment of the invention. A head 90 and all of the tooth cleaning elements projecting from the head are the same as shown in FIG. 1. A handle 92 encloses a 1.5 volt triple A battery 94 and a motor 96. An eccentrically mounted weight 98 is secured to a drive shaft 100 which projects from the motor. An on/off switch 102 projects slightly out of the handle.

When the on/off switch is depressed a first time, an electrical circuit between battery 94 and motor 96 is completed causing the motor to rotate shaft 100. The shaft preferably rotates at between about 9700-12,400 rpm. Weight 98 is thus also rotated. As the weight is eccentrically mounted, rotating the weight causes a vibration which is transmitted to handle 92, head 90 and the tooth cleaning elements on the head.

One type of motor which can be used is a P/N Q6DL-2.6A with a #17 counterweight attached. This motor was bought from Jin Long Machinery, 640 Dean Street, Brooklyn, N.Y. 11238 (718.783.2328). Also see www.vibramotor.com.

It should be noted that tooth cleaning elements 28 (FIG. 3) are oriented at an acute angle relative to that portion of a top surface of head 16 from which elements 28 project. In another embodiment of the invention, one or more of tooth cleaning elements 34, 36 and 38 can also be oriented at an acute angle to the top surface of head 16. The tooth cleaning elements can be oriented at two or more different angles and can also be angled in different directions such as along the length of the head, across the width of the head or part way between the length and width of the head (a compound angle). The tooth cleaning elements are preferably at an angle of between about 65-85 degrees measured from a line parallel or tangent to the top surface of the head.

All of tooth cleaning elements 28, 30, 34, 36 and 38 also have a non-circular cross-sections (see FIG. 2). Elements 30, 34 and 38 have cross-sections that can be described as a prolate ellipsoid with flattened long sides. Element 28 has a free end that defines a plane 28A which is non-perpendicular to a direction 28B in which element 28 extends away from head portion 20. The free end of element 28 can alternatively have a non-flat shape (e.g. curved) which can be formed by a hot tufting or spool feed tufting manufacturing process.

As shown in FIG. 3, the various tooth cleaning elements 28, 30, 34, 36 and 38 extend different heights above head 16. These elements also have several different cross-sections. In an alternative embodiment, the elements can also be at a number of different acute angles relative to the top surface of the head.

Further, one or more of these tooth cleaning elements can be replaced by a tooth cleaning element which is made of a thermoplastic elastomer. The thermoplastic elastomer tooth cleaning element can be a unitary structure, or it can be made up of a number of substructures. For example, the thermoplastic elastomer element could be a large unitary bristle (i.e. a nub) or it could have a number of smaller bristles (e.g. a tuft of bristles). The element could also be in the shape of a fin (as in FIG. 18), cup (e.g. prophy cup) or wall (curved or straight).

Different types of bristles which can be used on the toothbrush are bristles which (a) are tapered at their free end, (b) are flagged at their free end, (c) are hollow (see e.g. U.S. Pat. No. 5,836,769), (d) are crimped (see e.g. U.S. Pat. No. 6,058, 541), (e) have a cross-shaped or triangular cross-section, (f) are flocked, or (g) are notched (see e.g. U.S. Pat. No. 6,018, 840). Some of the bristles may include antibacterial agents, such as metal ions (e.g., silver, zinc, and silver zeolite) or cationic bactericides (e.g., chlorhexidine digluconate, and cetyl pyridinium chloride). Another example of a bristle that might be suitable for use is described in U.S. Pat. No. 5,633, 083. The anti-bacterial agents might also be disposed in any elements formed from an elastomer or other plastic material, including fins 80 and any of the composite structures described hereafter. Examples of some antibacterial agents, and other agents and materials, which can be used to form or be incorporated in the fins and composite structures are described in USPN 2003/0162145.

A tuft of bristles can alternatively have bristles made of different materials (e.g. some bristles made of nylon and other bristles made of polybutylene terepthalate) or bristles having different diameters.

Further, the plastic head can alternatively be covered partially or completely in a thermoplastic elastomer which acts to protect the teeth and gums from the plastic head. This results in a head made of two materials. Additional types of materials could also be provided on the head.

Figure 20:
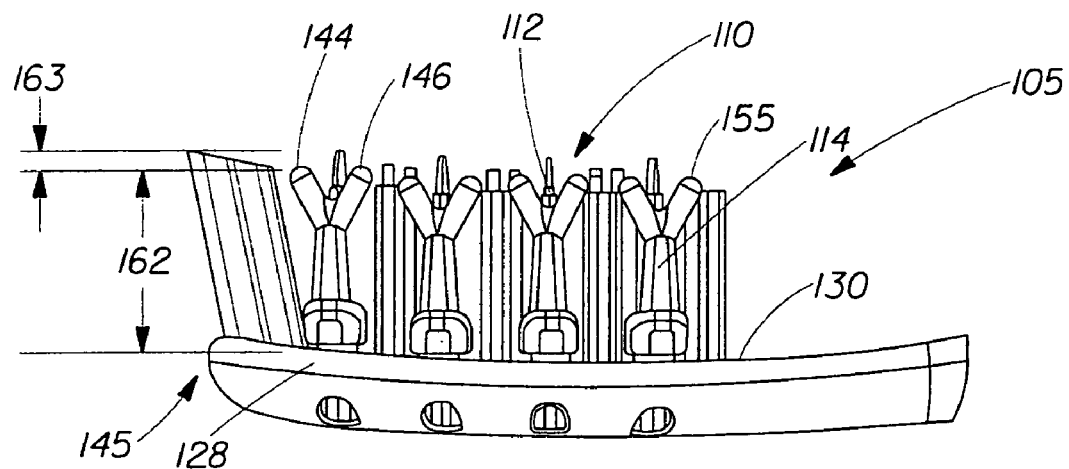
FIG. 20 is a side view of another embodiment of a head of the present invention.
Figure 21:
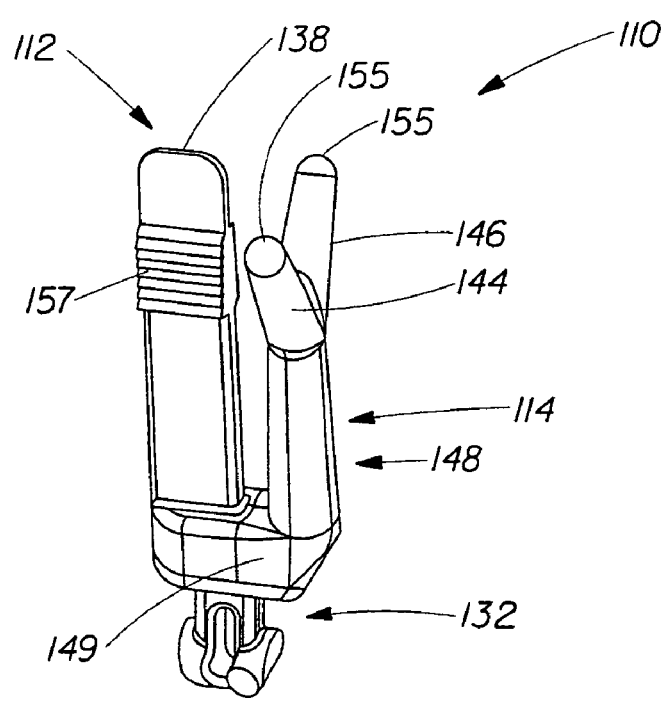
FIG. 21 is a perspective view of a composite structure of the present invention.
Figure 22:
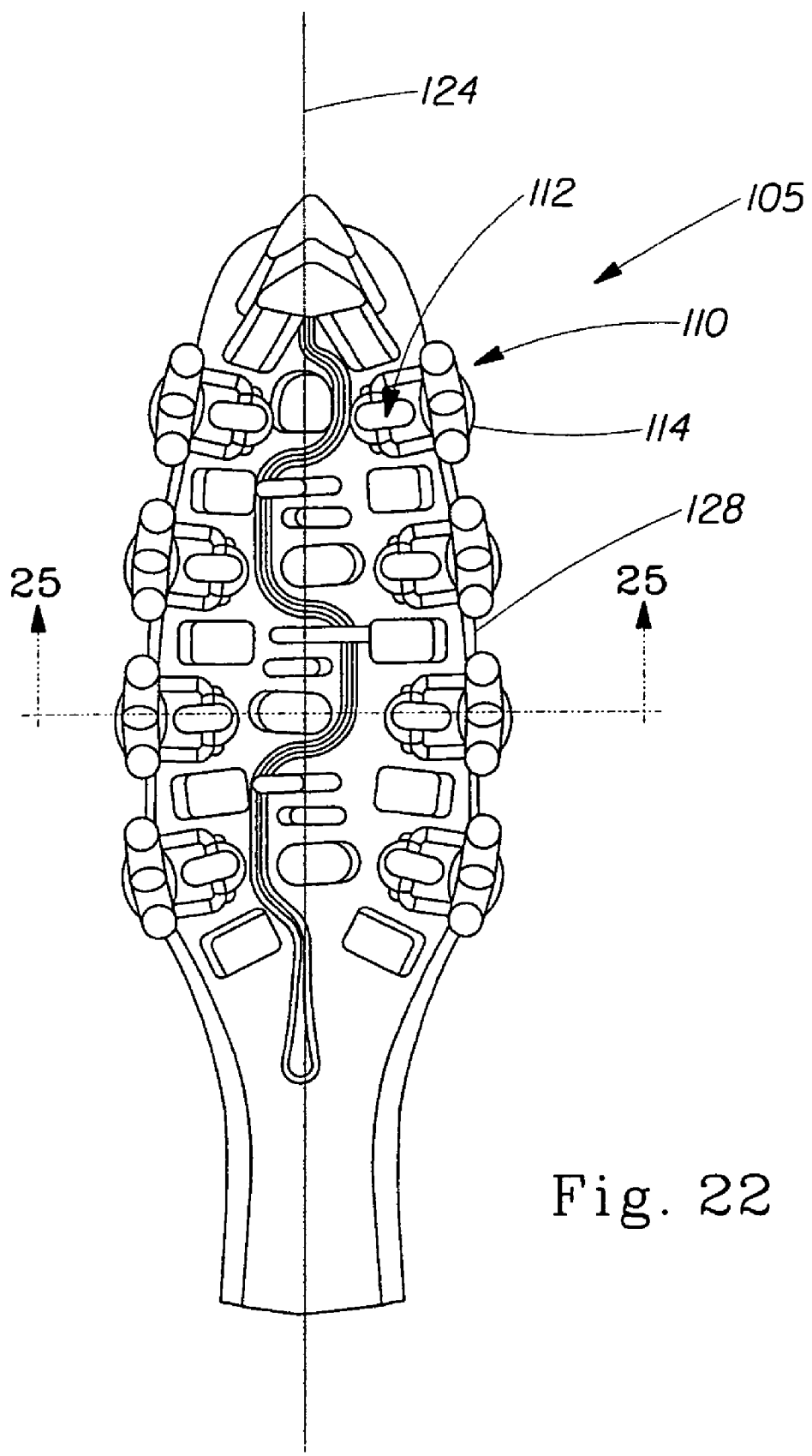
FIG. 22 is a top view of the head of FIG. 20.

Referring to FIGS. 20, 21, 22, 23, and 24, a toothbrush head 105 made in accordance with the present invention and suitable for use with the handle 92 of FIG. 19 will now be described. The toothbrush head 105 comprises one or more composite structures 110. The composite structure 110 of head 105 can comprise a first upstanding element 112 for contacting the teeth and a second upstanding element 114 spaced apart or offset from the first upstanding element 112 for contacting gum and other soft tissues adjacent the teeth. In one embodiment, the second upstanding element 114 is outwardly offset from the first upstanding element 112 in a direction away from the longitudinal axis 124 of the head 105. The second upstanding element 114 may be offset a distance 126 greater than about 0.4, 0.5, 0.6, 0.7, 0.8, 0.9, 1, or 1.1 mm and/or less than about 3, 2, 1.5, 1, 0.9, or 0.8 mm. The second upstanding element 114 may extend beyond the side surface 128 of the head 105 at least about 0.2, 0.4, 0.6, 0.8 mm and/or less than about 2, 1.6, 1.4, 1.2, 1, or 0.8 mm, as shown in FIG. 22. In other embodiments, the second upstanding element 114 does not extend beyond the side surface 128. The upstanding elements 112 and 114 extend upward or away from the top surface 130 of the head 105 as best seen in FIG. 20.

Figure 25:
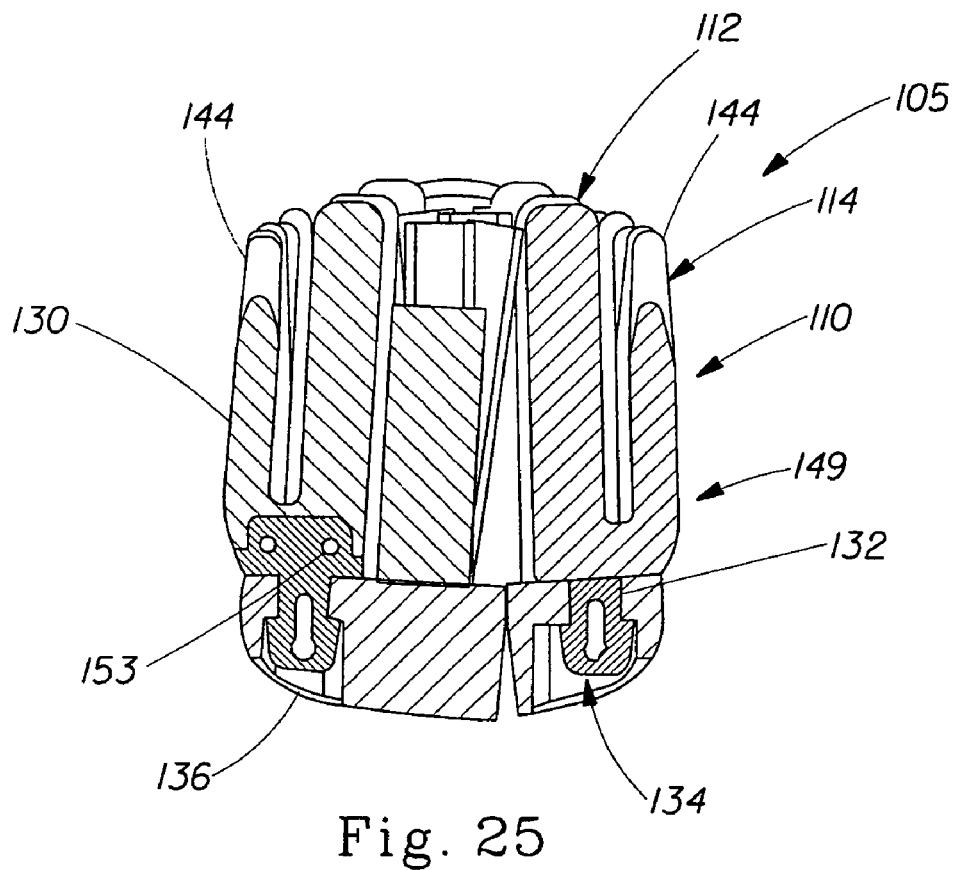
FIG. 25 is a cross-sectional front view of the head of FIG. 20, taken along 25-25 thereof.

The composite structure 110 also may comprise an anchor 132, which may be the same as or similar to the anchors 50 previously described. The anchors 132 may or may not be pivotably disposed within a hole 134 of the head 105. The hole 134 may extend wholly, or only partially, through the head 105 from the top surface 130 to the bottom surface 136, as shown in FIG. 25.

Figure 23:
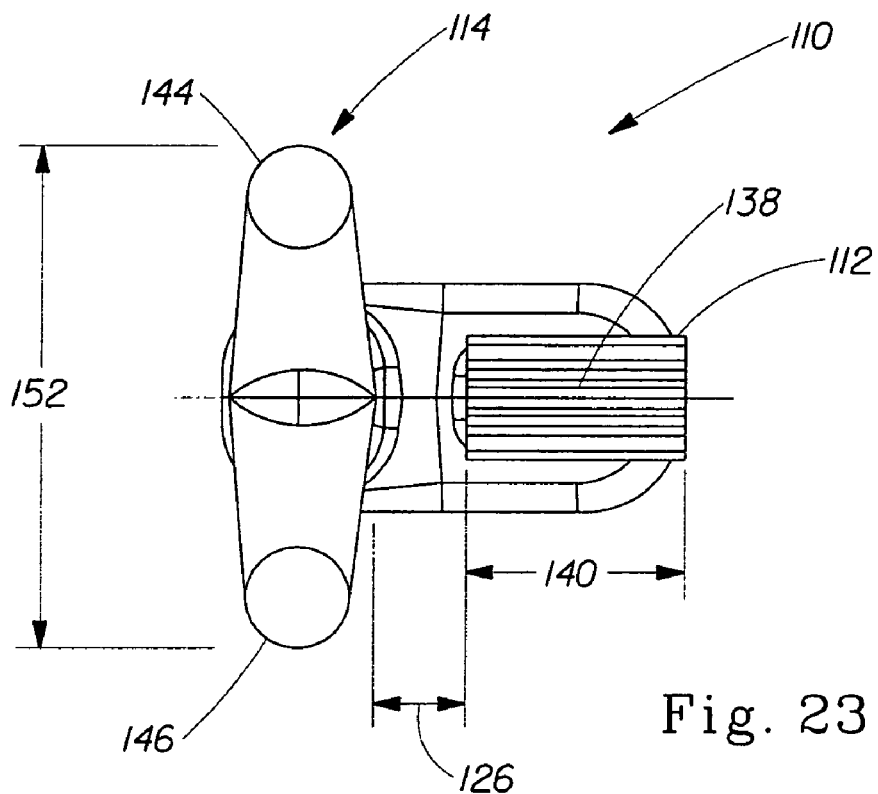
FIG. 23 is a top view of the composite structure of FIG. 21.

The first upstanding element 112 can be provided in a wide variety of shapes and sizes. In one embodiment, the first upstanding element 112 is provided in a form the same as or similar to the tufts 30 (FIG. FIG. 13) or fin 80 (FIG. 17) that have been previously described. For simplicity of discussion, the composite structures 110 discussed hereafter comprise a first upstanding element 112 in the form of a fin. The first upstanding element 112 has a tapered terminal end 138 having a long dimension 140 (FIG. 23). In one embodiment, the long dimension 140 of the terminal end 138 is arranged generally transverse or perpendicular to the longitudinal axis 124 of the head 105. This arrangement of the long dimension 140 of the first upstanding element 112 can be aid penetration of the terminal end 138 into interstitial tooth spaces.

Figure 24:
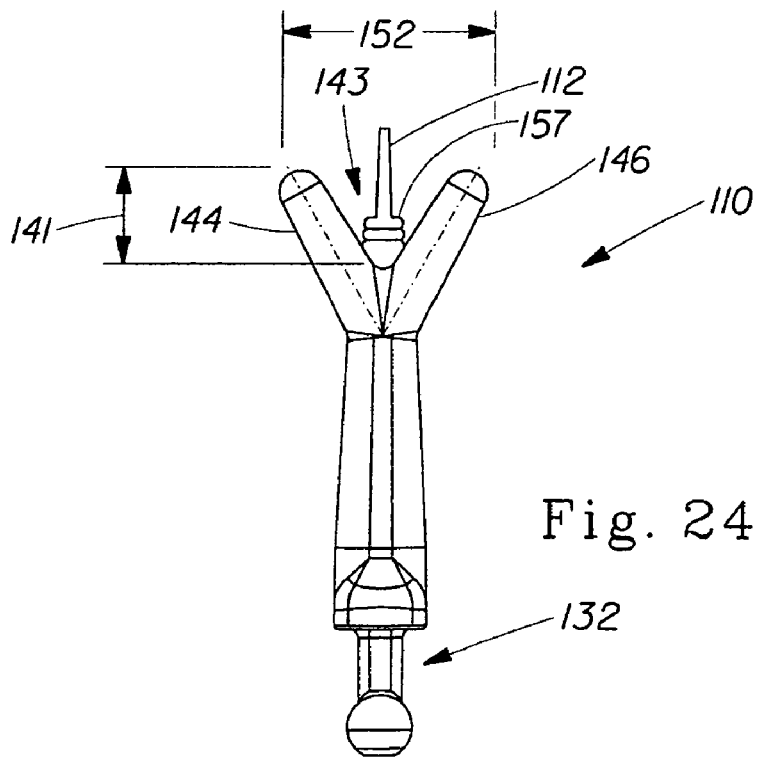
FIG. 24 is a side view of the composite structure of FIG. 21.

The second upstanding element 114 can also be provided in a wide variety of shapes and sizes. In one embodiment, the second upstanding element 114 comprises a first extension 144 and a second extension 146. The extensions may be spaced apart so that a gap 143 is formed therebetween. As shown in FIG. 24, the gap may have a depth 141 that is greater than about 1, 2, 3, 4, 5, 6, 7, or 8 mm and/or less than about 12, 11, 10, 9, 8, or 7 mm. While the second upstanding element 114 is shown with two extensions 144 and 146, it is contemplated that three, four, five, six or more extensions can be provided.

The first and second extensions 144 and 146 extend from a connecting element 148 of the second upstanding element 114. The connecting element 148 can be formed from the same material or different material as the extensions (144, 146) and/or the first upstanding element 112. While the connecting element 148 can be formed as a separate structure, it should be understood that connecting element 148 does not need to be a separately formed piece from the extensions and/or the first upstanding element 112. For example, as discussed below, the extensions 144, 146, the connecting element 148 and first upstanding element 112 can be integrally formed from the same material in or more injection molding steps. The connecting element 148 and/or first and second extensions, 146 and 148, may provide the second upstanding element 114 with a generally Y-shaped form in side view, as best seen in FIG. 20. The terminal end of the second upstanding element 114 has a long dimension 152 that is generally parallel with the longitudinal axis 124 of the head 105 and which is generally perpendicular to the long dimension 140 of the first upstanding element 112.

Figure 26:
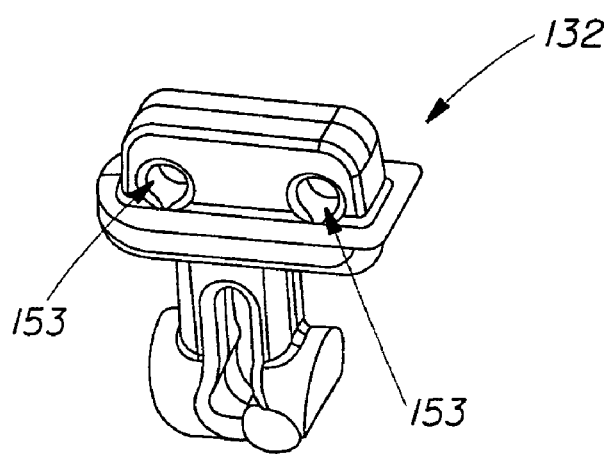
FIG. 26 is a perspective view of the anchor shown in FIG. 25.

In some embodiments, the second upstanding element 114 is connected or attached to the first upstanding element 112 above the top surface 130 of the head 105. In one embodiment, the connecting element 148 is connected or attached to the first upstanding element 112 and the anchor 132. The connecting element 148 has a portion 149 that may be generally parallel to the top surface 130 of the head 105, as shown in FIG. 25. The connecting element 148 may be attached to the first upstanding element 112 by mechanical, adhesive, and/or chemical means as known in the art and may be a separately formed piece or formed integrally with the first and second upstanding elements. The extensions and connecting element of the 148 of the second upstanding element 114 can be unitarily formed, such as by injection molding, from one or more materials. Some materials that may be suitable for use are disclosed in U.S. Pat. No. 5,987,688. In one embodiment, the connecting element 148 can be attached to the anchor 132 by injection molding the connecting element 148 around or through one or more holes 153 and/or protuberances of the anchor 132, as shown in FIG. 26.

The second upstanding element 114 may further comprise one or more spherical portions. A spherical portion is any portion in the general shape of at least a portion of a sphere, such as a hemisphere, quarter sphere, spherical segment, etc. As used herein, spherical portion is intended to encompass shapes that are not perfectly spherical (i.e., whose outer surface is formed from a constant radius) but which may, for example, have a surface formed from radii of different lengths so that a pure spherical surface, or portion thereof, is not formed. Spherical portions 155 may be located at the terminal end of the second upstanding element 114 (or the first upstanding element 112), such as shown by way of example in FIGS. 20, 21, and 27, or along one or more sides 156 of the extensions, such as shown by way of example in FIG. 30.

Figure 34:
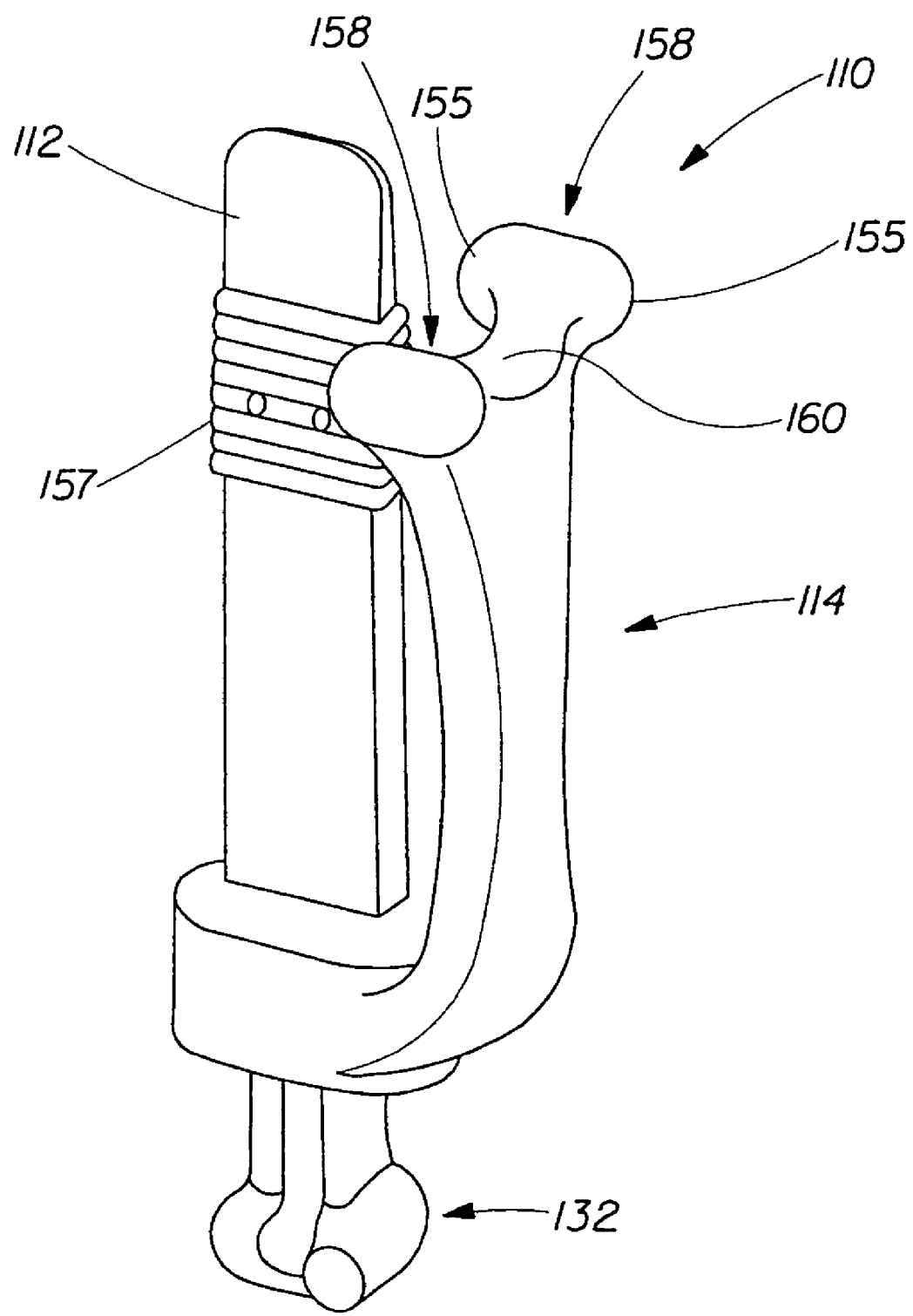
FIG. 34 is a perspective view of another composite structure of the present invention.

The second upstanding element 114 may further be provided in a variety of still other shapes and sizes. As shown in FIGS. 31 and 32, the second upstanding element 114 may also be provided in a general V or U shape in side view. As seen FIG. 34, in another embodiment, spherical portions 155 can form a plurality of opposed pill-shaped elements 158 with a curved terminal end portion 160 disposed therebetween. In still other embodiments, one or more of the extensions (e.g., 144, 146) may be angled toward the free end 145 of the head 105, as shown in FIG. 20, and/or toward the handle of the toothbrush, as shown in FIG. 20. One or more of the extensions 144 and 146 may be generally curved or curvilinear, some examples of which are shown in FIGS. 35, 36, wherein the extension is curved toward (FIG. 36) or away (FIG. 35) from the first upstanding element 112. In another instance, the second upstanding element 114 can be formed with a compound curve or a plurality of curves, as shown by way of example in FIGS. 39 and 40. In still other embodiments, one or more of the extensions may be curved toward the free end of the head (FIG. 38) or toward the handle (FIG. 37). In still other embodiments, one or more of the extensions may be generally pie-shaped (in side view), as shown by way of example in FIGS. 29, 30, and 33. The pie-shapes can have straight, concave, convex and other shaped sides.

The second upstanding elements 114 may be used to contact the soft tissues of the gums during use of the toothbrush, including gingival tissues such as the gingival margin, gingival sulculus, and the inter dental gingiva. As such, the second upstanding elements are placed adjacent the side surface 128 of the head 105. In some embodiments, the second upstanding elements 114 have a height 162 of at least about 5, 6, 7, 8, 9, 10, 11, 12 or 13 mm and/or less than about 15, 14, 13, 12, 11, 10, 9, or 8 mm. The portion of the terminal end of the second upstanding element 114 furthest from the top surface of the head may be disposed a distance 163 greater than about 0.5, 0.75, 1, 1.25, 1.5, 1.75, 2, 2.25, 2.5 mm and/or less than about 4, 3, 2.5, or 2 mm below the portion of the terminal end of the first upstanding element 112 furthest from the top surface of the head.

Figure 41:
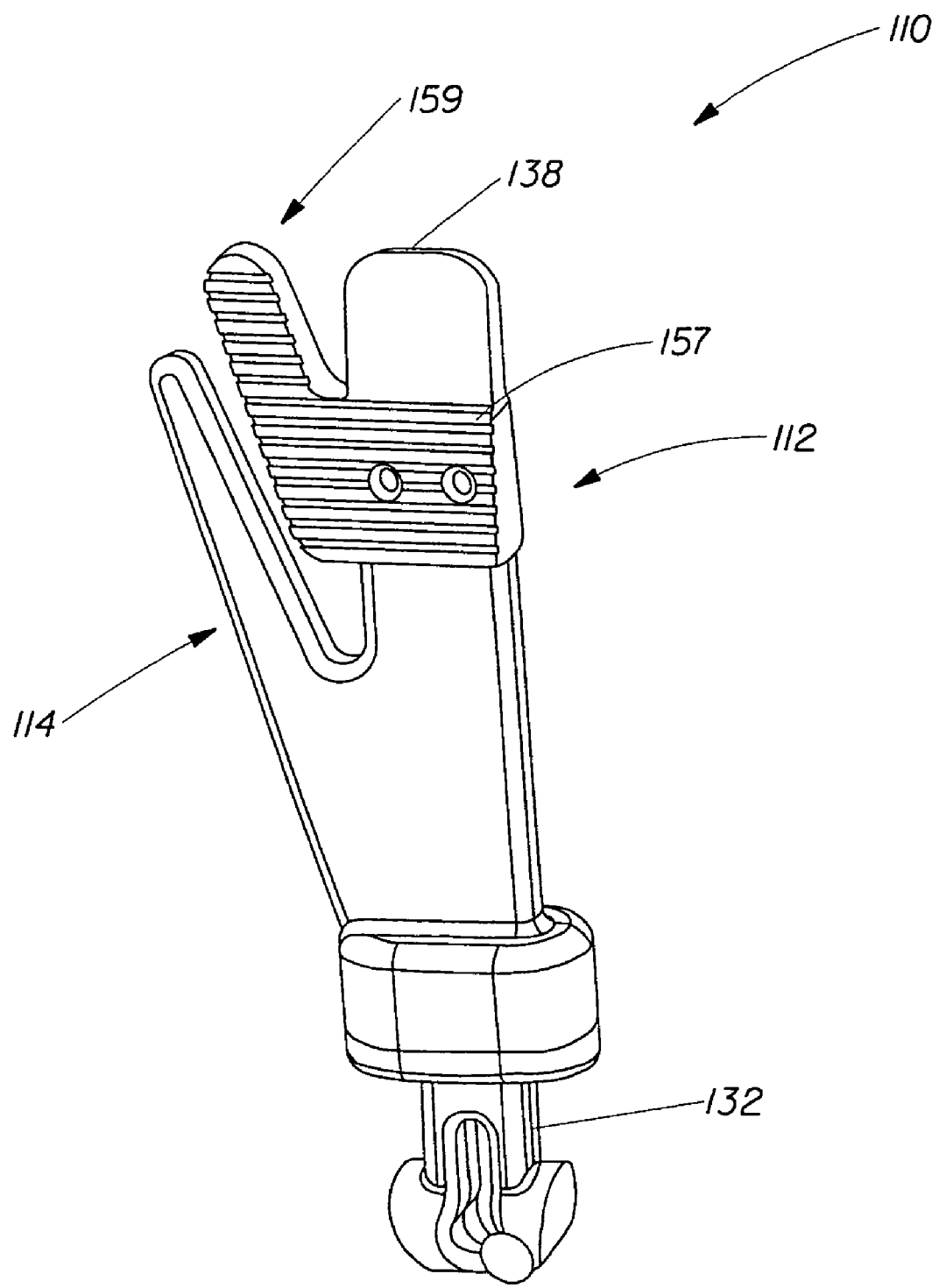
FIG. 41 is perspective view of another composite structure of the present invention.

While the first upstanding element 112 has been shown herein as a fin having a textured portion or pad 157, it is contemplated that the fin can be provided with an extension 159, as shown by way of example in FIGS. 39, 40, and 41. The extension 159 can extend from the textured portion 157 or from another location on the first upstanding element 112. The extension 159 can also be textured, including textures such as ribs, protrusions, pyramids, parallelpipeds, etc. The extensions can have any of the shapes previously discussed, including straight, angles, cylindrical, flat, curved, curvilinear, compound curving, etc. In some embodiments, the extension 159 begins greater than about 1, 2, 3, 4, 5, or 6 mm and/or less than about 8, 7, 6, 5, or 4 mm from the terminal end 138 of the first upstanding element 112. The extension 159 can be made from the same, or different material, as the first upstanding element 112 and/or the textured portion 157.

While the composite elements have been described herein with respect to a toothbrush having a motor for vibrating the head 105 (one arrangement suitable for vibrating the head being shown in FIG. 19 and other arrangements are described in U.S. Pat. No. 6,766,548 and 2006/0156496), it is contemplated that the composite elements can be provided on a manual toothbrush without a motor.

Figure 42:
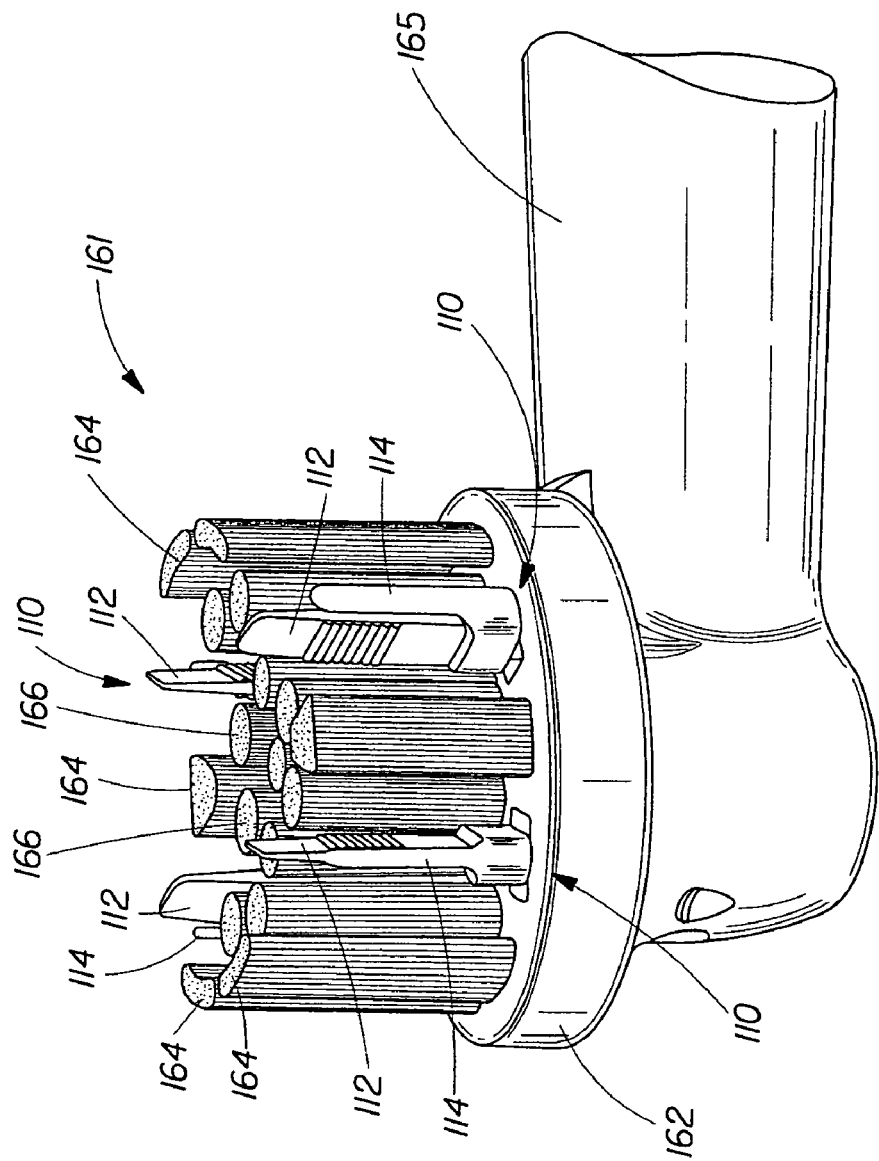
FIG. 42 is a perspective view of a rotatable head of the present invention.
Figure 43:
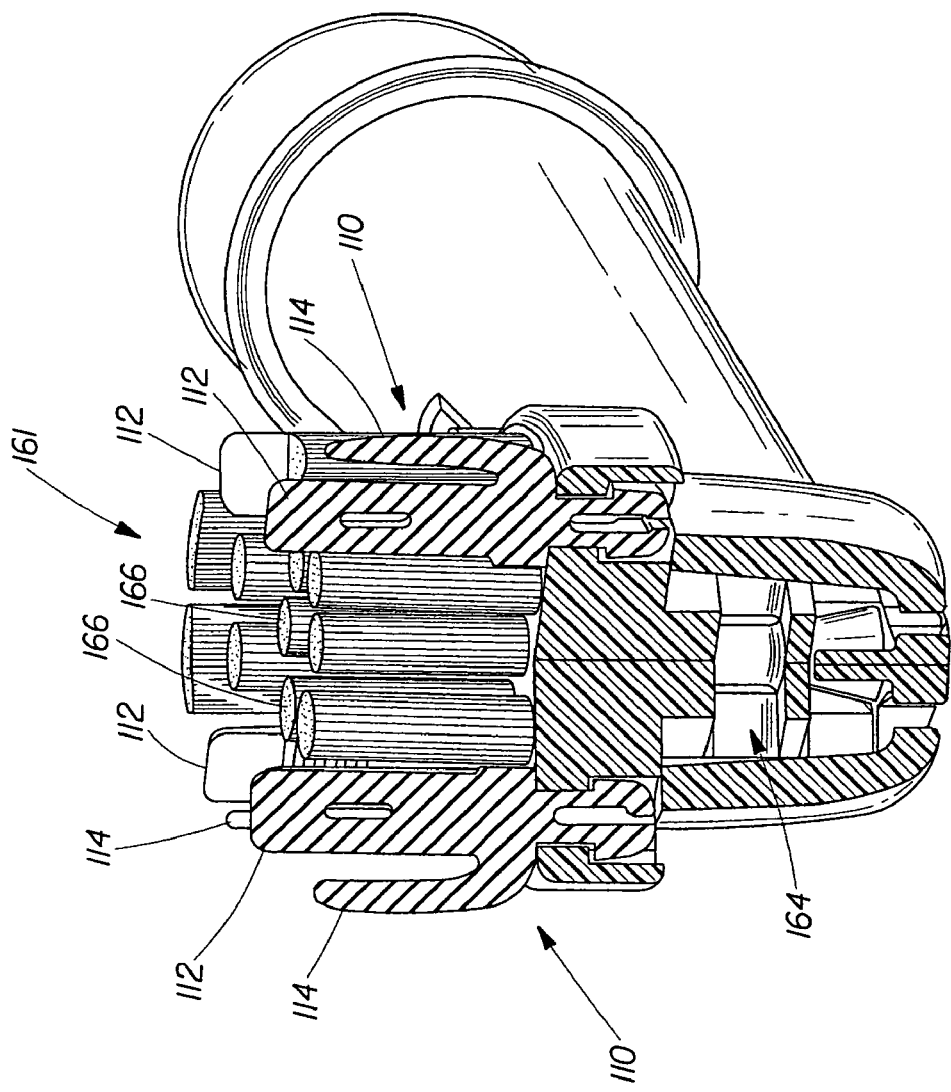
FIG. 43 is a cross-sectional perspective view of the rotatable head of FIG. 42.

Still in other embodiments, it is contemplated that the composite elements of the present invention can be provided on a rotating or oscillating support member, such as shown in FIGS. 42-45. A general description of support members that may be used with the present invention are presented in USPN 2005/0060822; 2004/0154112; U.S. Pat. Nos. 5,867,856; 5,862,558; 5,974,615; 1003/0131427; U.S. Pat Nos. 5,974,613; 6,195,828; and 6,367,108. As shown in FIGS. 42 and 43, the head 161 comprises a rotating or oscillating support member 162 that supports a plurality of bristle tufts 164 and a plurality of composite structures 110. The composite structures 110 may comprise a first upstanding element 112 in the form of a fin and a second upstanding element 114. The support member 162 may be operatively connected to a shaft (not shown) in the neck 165, which may or may not include gears. The shaft is operatively connected to a motor in the handle for driving the shaft, as is known in the art. The composite structures 110 may surround one or more central bristle tufts 166. The composite structures may be pivotally mounted in holes 134 as previously described.

Figure 44:
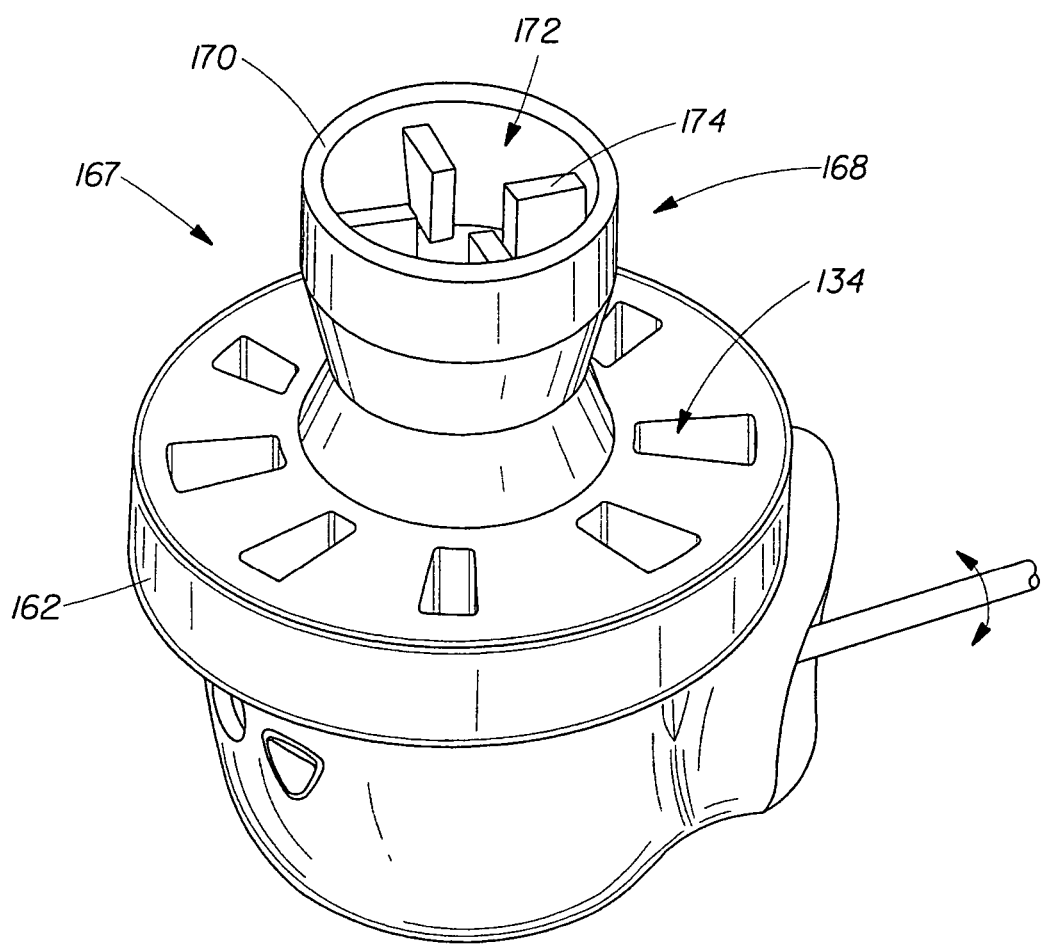
FIG. 44 is a perspective view of another rotatable head of the present invention.

As shown in FIG. 44, the central bristle tufts can be replaced by a cup-shaped member 168 (the composite structures 110 have been omitted for clarity). The cup-shaped member 168 of head 167 may be wholly, substantially, or partially surrounded by one or more of any of the composite structures 110 previously described. The cup-shaped member 168 includes a side wall 170 that defines a central area 172. The side wall may be provided in a variety of shapes and sizes, including cylindrical, conical, frusto-conical, etc. Generally, the central open area 172 has a depth of from about 2 to 5mm, measured from the highest point of the rim of the cup-shaped member to the lowest point of the central open area. In one embodiment, the cup-shaped member 168 also includes a plurality of ribs 174 that extend inwardly into the open area 172. The cup-shaped member 168 is preferably formed of a resilient material such as an elastomer (e.g., a thermoplastic elastomer). The material hardness for such structures may range from 10to 70 Shore A, with the preferred hardness selection depending on the design and dimensions of the cup-shaped member. The support member 162 may be rotatably mounted so that the cup-shaped member 168 can rotate or oscillate.

Figure 45:
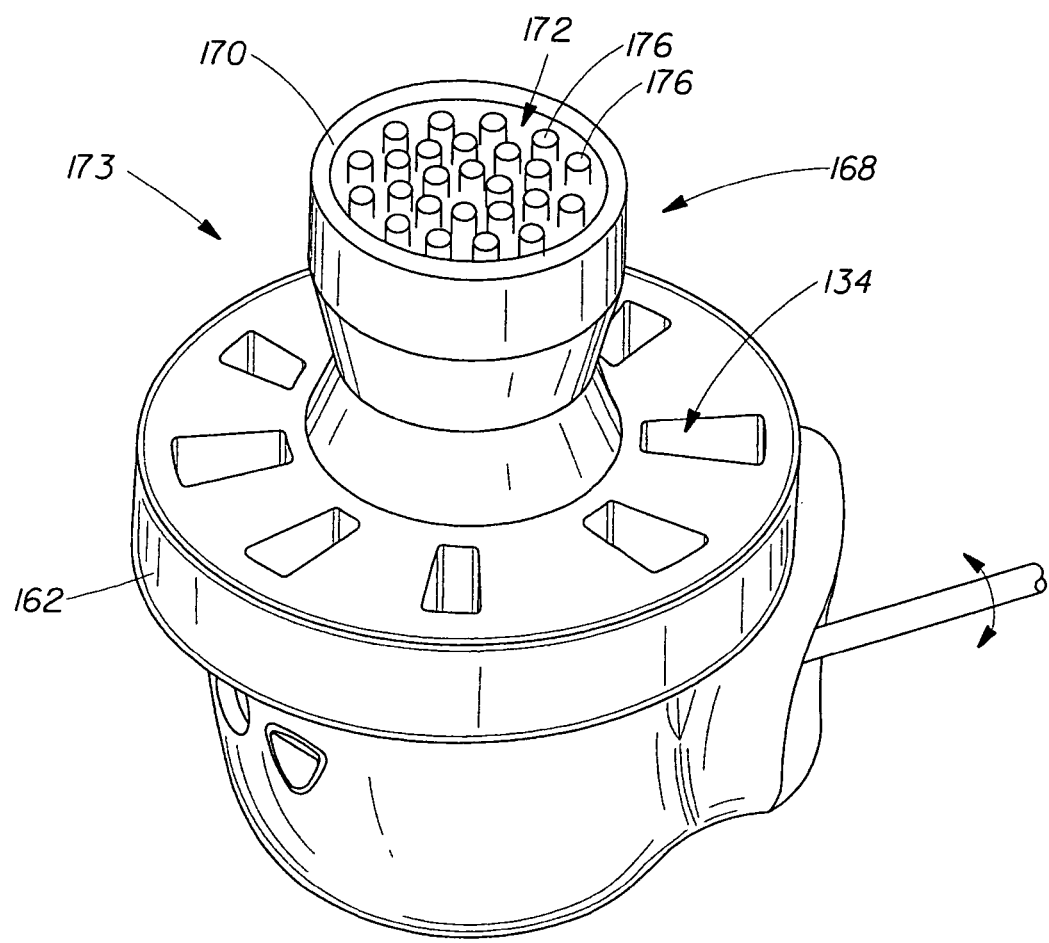
FIG. 45 is a perspective view of another rotatable head of the present invention.

Referring to FIG. 45, another embodiment of the cup-shaped member 168 is shown on head 173. The central area 172, which may be open or closed, has a plurality of generally cylindrical elements or cilia 176 that extend upwardly from the central area 172. The cylindrical elements may be formed from a variety of materials, including elastomeric materials. They may be formed from the same material that forms the side wall 170 of the cup shaped element 168. In one embodiment, the heads 167 and 173 of FIGS. 39 and 40 utilize cleaning elements that are only formed from elastomeric materials and do not contain tufts of traditional bristles (e.g., formed from NYLON or PBT). The elastomeric cleaning elements may be provided in a variety of shapes and sizes and may partially or wholly surround the elastomeric cup-shaped member. The elastomeric cleaning elements may be provided in a form as described herein (e.g., composite structures 110 or fin 80) or may be provided in other forms, some examples of which are described in U.S Pat. Nos. 6,886,207 and 5,987, 688. In another embodiment, the heads 167 and 173 shown in FIGS. 44 and 45 may be provided with a plurality of tufts of traditional bristles which may, or may not, be provided in combination with one or more composite structures 110, pivoting tufts 30 (FIG. 9), and/or pivoting fin 80 (FIG. 17). Other cup-shaped members 168 that may be suitable for use are further described in USPN2004/0154112.

Figure 46:
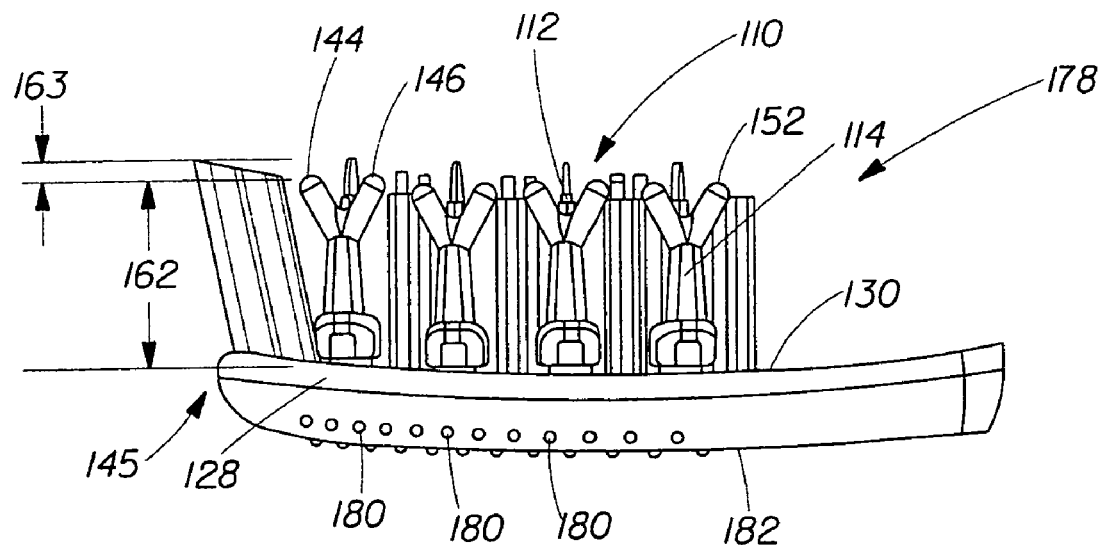
FIG. 46 is a side view of a head of the present invention incorporating a plurality of tissue treating elements on the rear or bottom surface of the head.
Figure 47:
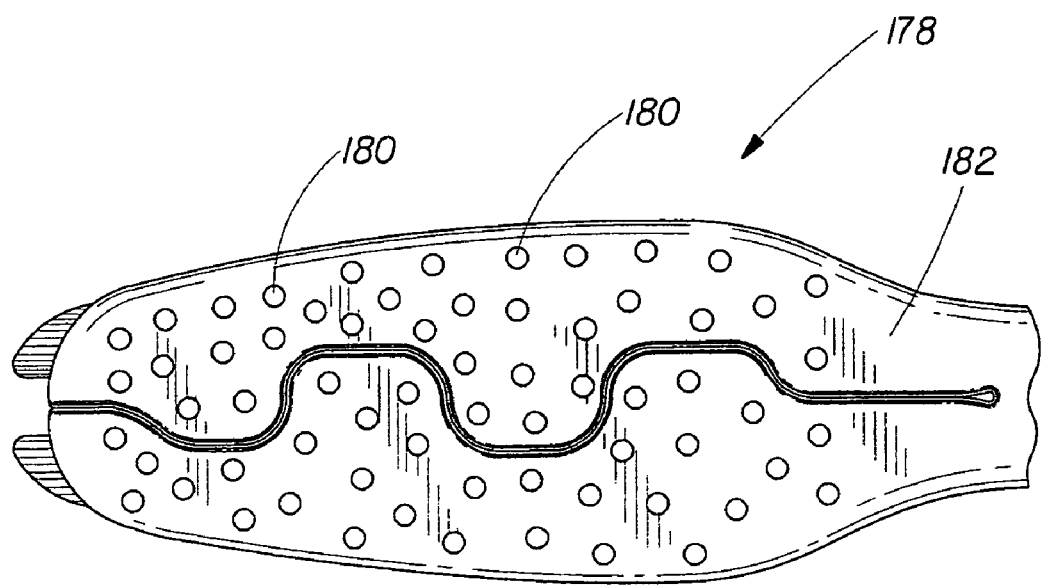
FIG. 47 is a bottom view of the head of FIG. 46.

The toothbrushes of the present invention may also incorporate tissue cleaning elements on the rear surface of the head. For example, referring to FIGS. 46-48, a toothbrush head 178 has one or more soft tissue treating elements 180, shown as hemispherical elements, on the rear surface 182 of the head 178. The soft tissue treating structures can be used to scrub, scrape, stimulate, and/or massage the surfaces of the tongue. The soft tissue treating elements 180 can be provided in a variety of shapes and sizes, including conical, pyramidal, hemispherical, frusto-conical, etc. Some examples of other tissue treating or tongue treating elements are described in USPNs 2006/0195995and 2006/0129171. The head 178 may also optionally incorporate one or more composite structures 110, pivoting tufts 30, pivoting fins 80 and/or traditional tufts of bristles that have been previously described or as known in the art. These surfaces or elements may be overmolded onto the head 178 to form a portion of, or all of, the rear surface 182 of the head 178.

Figure 48:
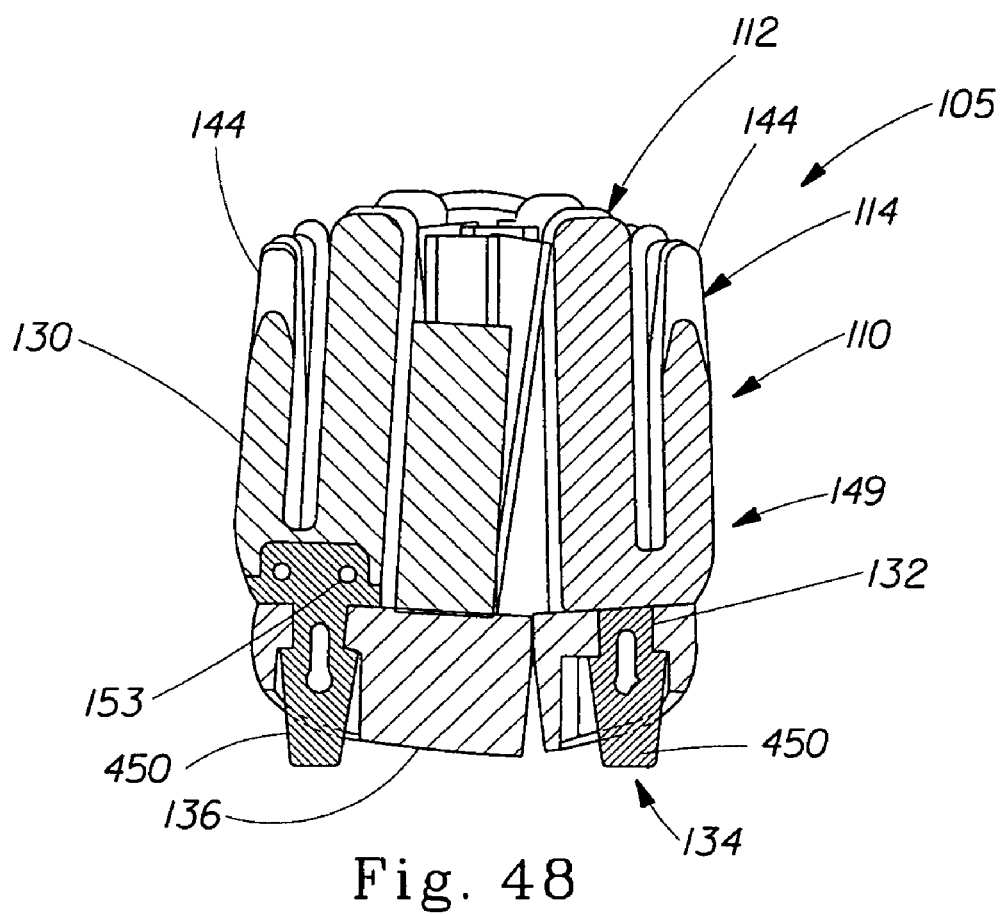
FIG. 48 is a cross-sectional front view of a head of a toothbrush constructed in accordance with the present invention, the section line being similar to that shown for FIG. 20, taken along 25-25 thereof.

With regard to FIG. 48, embodiments are contemplated where a portion of the composite structure 110 extends through the hole 134 of the head 105. As shown, in some embodiments, a terminal end 450 of the anchor 132 may extend through the hole 134 in the head 105 and form a portion of the soft tissue treating elements 180 (shown in FIGS. 46 and 47). The terminal ends 450 of the anchor 132 may terminate in a flap, a ball, a wave, an arc, or any suitable shape. Additionally, as mentioned previously, the composite structures 110 may be pivotally disposed with respect to the head 105. As such, in some embodiments, the terminal ends 450 may similarly be pivotable with respect to the head 105.

While the various tooth cleaning elements, gum treating elements, and soft tissue cleaning elements have been illustrated herein with a head attached to a toothbrush handle, it is contemplated that replaceable toothbrush heads may also incorporate one or more of these features and be packaged or distributed without the corresponding toothbrush handle.

The invention has been described with reference to a preferred embodiment. However, it will be appreciated that variations and modifications can be effected by a person of ordinary skill in the art without departing from the scope of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush comprising:
   a handle;
   a head connected to the handle, the head having a rotatable support member, the support member having;
      a top surface, a bottom surface opposite the top surface, and a side surface between the top surface and the bottom surface;
      at least one composite structure comprising a first upstanding element and a second upstanding element, wherein the first upstanding element is connected to the second upstanding element, the at least one composite structure being disposed adjacent to the side surface of the support member and wherein the second upstanding element is outwardly offset from the first upstanding element in a direction away from the center of the support member, wherein the second upstanding element has a shape generally in the form of a V; and
      a plurality of cleaning elements disposed inboard of the side surface of the support member.

2. The toothbrush of claim 1, wherein a hole disposed in the top surface is adjacent the side surface, wherein at least a portion of an anchor is received within the hole, and wherein the anchor is attached to the first upstanding element and the second upstanding element.

3. The toothbrush of claim 2, wherein the anchor is pivotably disposed within the hole.

4. The toothbrush of claim 1, wherein at least a portion of the second upstanding element extends beyond the side surface of the support member.

5. The toothbrush of claim 1, wherein the first upstanding element is a fin and wherein the first upstanding element is distinct from the second upstanding element.

6. The toothbrush of claim 1, further comprising a plurality of composite structures.

7. The toothbrush of claim 1, further comprising a motor for moving support member of the head.

8. The toothbrush of claim 1, wherein the first upstanding element and the second upstanding element are offset by greater than about 1.1mm 9. The toothbrush of claim 1, further comprising a connecting element connecting the first upstanding element and the second upstanding element.

10. The toothbrush of claim 9, wherein the connecting element, the first upstanding element and the second upstanding element are integrally formed.

11. The toothbrush of claim 10, wherein the connecting element, the first upstanding element and the second upstanding element comprise a thermoplastic elastomer.

12. A toothbrush head comprising:
   a rotatable support member, the support member having;
      a top surface, a bottom surface opposite the top surface, and a side surface between the top surface and the bottom surface;
      at least one composite structure comprising a first upstanding element and a second upstanding element, wherein the first upstanding element is connected to the second upstanding element, the at least one composite structure being disposed adjacent to the side surface of the support member and wherein the second upstanding element is outwardly offset from the first upstanding element in a direction away from the center of the support member, wherein the second upstanding element has a shape generally in the form of a V; and
      a plurality of cleaning elements disposed inboard of the side surface of the support member.

13. The toothbrush head of claim 12, wherein a hole disposed in the top surface is adjacent the side surface, wherein at least a portion of an anchor is received within the hole, and wherein the anchor is attached to the first upstanding element and the second upstanding element.

14. The toothbrush head of claim 13, wherein the anchor is pivotably disposed within the hole.

15. The toothbrush head of claim 12, wherein at least a portion of the second upstanding element extends beyond the side surface of the support member.

16. The toothbrush head of claim 12, wherein the first upstanding element is a fin and wherein the first upstanding element is distinct from the second upstanding element.

17. The toothbrush head of claim 12, further comprising a plurality of composite structures.

18. The toothbrush head of claim 12, wherein the first upstanding element and the second upstanding element are offset by greater than about 1.1 mm 19. The toothbrush head of claim 12, further comprising a connecting element connecting the first upstanding element and the second upstanding element.

20. The toothbrush head of claim 19, wherein the connecting element, the first upstanding element and the second upstanding element are integrally formed.

21. The toothbrush head of claim 20, wherein the connecting element, the first upstanding element and the second upstanding element comprise a thermoplastic elastomer.

* * * * *